United States Patent [19]

Simon et al.

[11] Patent Number: 4,863,949
[45] Date of Patent: Sep. 5, 1989

[54] AMINOPROPANOL DERIVATIVES, PROCESSES FOR THE PREPARATION THEREOF, THE USE THEREOF AND PHARMACEUTICAL COMPOSITIONS CONTAINING THEM

[75] Inventors: Herbert Simon, Lampertheim; Helmut Michel, Mannheim; Wolfgang Bartsch, Vierheim; Klaus Strein, Hemsbach, all of Fed. Rep. of Germany

[73] Assignee: Boehringer Mannheim GmbH, Mannheim, Fed. Rep. of Germany

[21] Appl. No.: 98,719

[22] Filed: Sep. 21, 1987

Related U.S. Application Data

[63] Continuation of Ser. No. 846,257, Mar. 31, 1986, abandoned.

[30] Foreign Application Priority Data

Apr. 6, 1985 [DE] Fed. Rep. of Germany ....... 3512627

[51] Int. Cl.[4] .................. C07D 209/34; C07D 209/30; C07D 209/08; C07D 211/40; C07D 223/08; A61K 31/40; A61K 31/445; A61K 31/55

[52] U.S. Cl. ..................................... 514/418; 548/469; 548/483; 548/484; 548/485; 548/486; 548/491; 548/493; 548/503; 548/505; 548/305; 548/325; 548/329; 548/327; 548/330; 548/444; 546/201; 546/146; 546/150; 546/157; 546/158; 546/221; 540/602; 514/212; 514/323; 514/414; 514/415; 514/419; 514/224.2; 514/259; 514/307; 514/312; 514/319; 514/387; 514/394; 514/395; 514/456; 514/457; 514/465; 514/509; 514/470; 514/434; 544/52; 544/286; 549/15; 549/289; 549/408; 549/438; 549/464; 549/465; 549/512; 549/551; 549/555; 558/414; 558/482; 558/483; 558/484; 560/169; 564/123; 564/201

[58] Field of Search ............... 514/415, 418, 419, 212, 514/323, 414; 548/469, 484, 486, 490, 491, 483, 485, 493, 503, 505; 540/602; 546/201

[56] References Cited

U.S. PATENT DOCUMENTS

| | | |
|---|---|---|
| 3,644,469 | 2/1972 | Köppe et al. ................ 558/408 |
| 3,911,136 | 10/1975 | Ferrari ........................ 514/509 |
| 3,928,412 | 12/1975 | Smith .......................... 564/189 |
| 4,086,357 | 4/1978 | Large et al. ................ 514/620 |
| 4,288,452 | 9/1981 | Sombroek et al. ......... 558/482 |
| 4,419,363 | 12/1983 | Smith .......................... 514/317 |

FOREIGN PATENT DOCUMENTS

| | | | |
|---|---|---|---|
| 3426419 | 1/1986 | Fed. Rep. of Germany | 548/486 |
| 0077257 | 6/1981 | Japan ........................ | 514/415 |
| 7208332 | 12/1972 | Netherlands .............. | 514/418 |
| 0636856 | 6/1983 | Switzerland ............... | 514/415 |
| 2044251 | 10/1980 | United Kingdom ....... | 514/466 |

OTHER PUBLICATIONS

Ahlmark et al., *The Lancet*, p. 1563, (12/28/74).
Ahlmark et al., *Europ. J. Clin. Pharmacol.*, , 10, pp. 77-83, (1976).
Chamberlain et al., *Postgraduate Medical Journal*, 52, (Suppl. 4), pp. 153-154, (1976).
Bartsch et al., *Drug Research*, 27, pp. 2319-2322, (1977).
Abstract for Japan Patent No. 56/077257, (6/25/81).
Derwent Abstract #86-029678/05 for DE Patent No. 3426419, (1/23/86), (1986).
Abstract for Swiss Patent No. 636856, (6/30/83).

*Primary Examiner*—Anton H. Sutto
*Assistant Examiner*—E. Bernhardt
*Attorney, Agent, or Firm*—Felfe & Lynch

[57] ABSTRACT

The present invention provides compounds of the general formula:

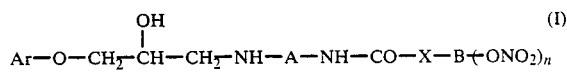

$$Ar-O-CH_2-\underset{\underset{OH}{|}}{CH}-CH_2-NH-A-NH-CO-X-B+ONO_2)_n \quad (I)$$

wherein Ar is a substituted or unsubstituted aromatic or heteroaromatic radical, A is a straight-chained or branched alkylene chain containing up to 8 carbon atoms, a —CH$_2$— group of which can be replaced by a cycloalkylene radical containing 3 to 7 carbon atoms, B is a straight-chained mono- or bicyclic, optionally branched, saturated or unsaturated alkylene chain containing up to 12 carbon atoms, a —CH$_2$— group of which can be replaced by a cycloalkylene radical containing 3 to 7 carbon atoms and/or up to two —CH$_2$— groups of which can be replaced by an oxygen or a sulphur atom or by an —S(=O) or —S(=O)$_2$ group, X is a valency bond, an oxygen atom or an —NR$^1$ group, in which R$^1$ is a hydrogen atom or a straight-chained or branched, saturated or unsaturated alkyl or nitroxyalkyl radical containing up to 6 carbon atoms or R$^1$, together with the nitrogen atom of the —NR$^1$— group and a —CH$_2$— group of the chain B, can form a heteroaliphatic ring containing 4 to 6 carbon atoms and n is 1, 2 or 3; and the physiologically acceptable salts thereof. The present invention also provides processes for the preparation of these compounds and pharmaceutical compositions containing them. Furthermore, the present invention is concerned with the use of these compounds for the treatment and/or prophylaxis of heart and circulatory diseases.

15 Claims, No Drawings

AMINOPROPANOL DERIVATIVES, PROCESSES FOR THE PREPARATION THEREOF, THE USE THEREOF AND PHARMACEUTICAL COMPOSITIONS CONTAINING THEM

This application is a continuation, of application Ser. No. 846,257, filed Mar. 31, 1986, now abandoned.

The present invention is concerned with new aminopropanol derivatives, processes for the preparation thereof, the use thereof and pharmaceutical compositions containing them.

Thus, according to the present invention, there are provided aminopropanol derivatives of the general formula:

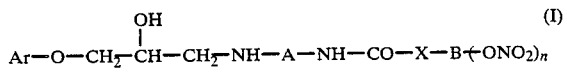

$$Ar-O-CH_2-\overset{OH}{\underset{|}{CH}}-CH_2-NH-A-NH-CO-X-B(-ONO_2)_n \quad (I)$$

wherein Ar is a substituted or unsubstituted aromatic or heteroaromatic radical, A is a straight-chained or branched alkylene chain containing up to 8 carbon atoms, a —CH$_2$— group of which can be replaced by a cycloalkylene radical containing 3 to 7 carbon atoms, B is a straight-chained, mono- or bicyclic, optionally branched, saturated or unsaturated alkylene chain containing up to 12 carbon atoms, a —CH$_2$— group of which can be replaced by a cycloalkylene radical containing 3 to 7 carbon atoms and/or up to 2 —CH$_2$— groups of which can each be replaced by an oxygen or sulphur atom or by a —S(=O)— or —S(=O)$_2$ group, X is a valency bond, an oxygen atom or an —NR$^1$— radical, in which R$^1$ is a hydrogen atom or a straight-chained or branched, saturated or unsaturated alkyl or nitroxyalkyl radical containing up to 6 carbon atoms or R$^1$, together with the nitrogen atom of the —NR$^1$— radical and a —CH$_2$— group of the chain B, can form a heteroaliphatic ring containing 4 to 6 carbon atoms and n is 1, 2 or 3; and the physiologically acceptable salts thereof.

The radical Ar can be a phenyl radical which is unsubstituted or optionally mono- or polysubstituted. As substituents, there are mentioned, by way of example, halogen, cyano, hydroxy, amino, oxo, nitro, carboxyl, carbamoyl, trifluoromethyl, alkyl, alkenyl, alkynyl, cycloalkyl, bicycloalkyl, alkanoyl, alkoxy, alkoxyalkyl, alkoxyalkoxyalkyl, alkoxyalkoxy, alkenyloxy, alkenyloxyalkyl, alkynyloxy, alkynyloxyalkyl, cycloalkoxy, alkylthio, alkylthioalkyl, acylamino, acylaminoalkyl, acyloxy, alkoxycarbonyl, cycloalkyloxycarbonyl, alkylaminocarbonylamino, dialkylaminocarbonylamino, dialkylaminocarbonylaminoalkyl, dialkylaminocarbonylalkyl, dialkylaminocarbonylalkoxy, whereby, in the case of the four last-mentioned radicals, the two terminal alkyl moieties, together with the nitrogen atom to which they are attached, can also form a cyclic radical containing 4 or 5 carbon atoms, cycloalkylaminocarbonylamino, alkylaminocarbonylaminoalkyl, cycloalkylaminocarbonylaminoalkyl, alkoxycarbonylaminoalkyl, cycloalkoxycarbonylaminoalkyl, carbamoylalkyl, alkylaminocarbonylalkyl, cycloalkylaminocarbonylalkyl or alkylaminocarbonylalkoxy radicals.

Furthermore, the radical Ar can be a naphthyl, indenyl, indolyl, indazolyl, imidazolyl, benzimidazolyl, benztriazolyl, benzofuranyl, benzdioxolyl, benzothiophenyl, benzthiazolyl, benzisothiazolyl, quinolyl, isoquinolyl, benzodiazinyl, benzopyranyl, benzothiinyl, benzothiazinyl, benzothiadiazinyl, benzoxathiinyl, benzoxazolyl, benzisoxazolyl or carbazolyl radical, whereby one or more double bonds can be hydrogenated and these radicals can be unsubstituted or optionally mono- or polysubstituted. As substituent, there are mentioned, by way of example, alkyl, cyano, hydroxyalkyl, hydroxy, oxo, formyl, alkanoyl and alkylcarbonylamino radicals.

The phenyl radical can preferably be substituted once (especially in the o-position and in the p-position but also in the m-position) or twice (especially in the 2,5-position but also, for example, in the 2,3-, 2,4-, 3,4- or 3,5-position. However, it can also be substituted three times (especially in the 3,4,5-position but also, for example, in the 2,3,4-, 2,3,5- or 2,4,5-position), four times (for example in the 2,3,4,5-position) or five times. Preferred substituents in the phenyl radical include, in particular, F, Cl, Br, J; CN; OH; NH$_2$; NO$_2$; COOH; CONH$_2$, CF$_3$; alkyl with 1-10 and preferably 1-4 carbon atoms preferably methyl or ethyl, as well as, for example, n-propyl, isopropyl, n-butyl, isobutyl, sec.-butyl, tert.-butyl, pentyl, such as n-pentyl, hexyl, such as n-hexyl, heptyl, such as n-heptyl, octyl, such as n-octyl, nonyl, such as n-nonyl, or decyl, such as n-decyl; alkenyl with up to 10 and preferably 2-4 carbon atoms, for example vinyl, allyl, propenyl, isopropenyl, butenyl, such as but-1-en-1-, -2-, -3- or -4-yl, but-2-en-1-yl, but-2-en-2-yl, pentenyl, hexenyl or decenyl; alkynyl with up to 10 and preferably 2-4 carbon atoms, for example ethynyl, prop-1-yn-1-yl, propargyl, butynyl, such as but-2-yn-1-yl, pentynyl, decynyl; cycloalkyl with 3-8 and preferably 5 or 6 carbon atoms, especially cyclopentyl or cyclohexyl, as well as, for example, cyclopropyl, cyclobutyl, 1-, 2- or 3-methylcyclopentyl, 1-, 2-, 3- or 4-methylcyclohexyl, cycloheptyl or cyclooctyl; bicycloalkyl with 4-11 and preferably 7 carbon atoms, preferably exo- or endo 2-norbornyl, as well as, for example, 2-isobornyl- or 5-camphyl; alkanoyl with 1-7 and preferably 1-4 carbon atoms, preferably formyl, acetyl or propionyl, as well as, for example, butyryl, isobutyryl, valeroyl, caproyl, heptanoyl; alkoxy with 1-10 and preferably 1-4 carbon atoms, preferably methoxy or ethoxy, as well as, for example, n-propoxy, isopropoxy, n-butoxy, isobutoxy, sec.-butoxy, tert.-butoxy, pentyloxy, hexyloxy, heptyloxy, octyloxy, nonyloxy or decyloxy; alkoxyalkyl with up to 10 and preferably 2-6 carbon atoms, for example alkoxymethyl, such as methoxymethyl, alkoxyethyl, such as 1- or 2-methoxyethyl, 1- or 2-n-butoxyethyl, 1- or 2-n-octyloxyethyl; alkoxyalkoxyalkyl with up to 10 and preferably 4-7 carbon atoms, for example alkoxyalkoxymethyl, such as 2-methoxyethoxymethyl, 2-ethoxyethoxymethyl or 2-isopropoxyethoxymethyl; alkoxyalkoxyethyl, such as 2-(2-methoxyethoxy)-ethyl or 2-(2-ethoxyethoxy)-ethyl; alkoxyalkoxy with up to 10 and preferably 3-6 carbon atoms, for example 2-methoxyethoxy, 2-ethoxyethoxy or 2-n-butoxyethoxy; alkenyloxy with up to 10 and preferably 2-4 carbon atoms, preferably allyloxy, as well as, for example, vinyloxy, propenyloxy, isopropenyloxy, butenyloxy, such as but-1-en-1-, -2-, -3- or 4-yloxy, but-2-en-1-yloxy, but-2-en-2-yloxy, pentenyloxy, hexenyloxy or decenyloxy; alkenyloxyalkyl with up to 10 and preferably 3-6 carbon atoms, for example allyloxymethyl; alkynyloxy with up to 10 and preferably 2-4 carbon atoms, preferably propargyloxy, as well as, for example, ethynyloxy, prop-1-yn-1-yloxy, butynyloxy, such as but-2-yn-1-yloxy, pentynyloxy or decynyloxy; alkynyloxyalkyl with up to 10 and preferably 3–6 carbon atoms, for example ethynyloxymethyl, propargyloxymethyl or 2-(but-2-yn-1-yloxy)-ethyl; cycloalkoxy with 3–8 and preferably 5 or 6 carbon atoms, preferably cyclopentyloxy or cyclohexyloxy, as well as, for example, cyclopropyloxy, cyclobutyloxy, 1-, 2- or 3-methylcyclopentyloxy, 1-, 2-, 3- or 4-methylcyclohexyloxy, cycloheptyloxy or cyclooctyloxy; alkylthio with 1–10 and preferably 1–4 carbon atoms, preferably methylthio or ethylthio, as well as, for example, n-propylthio, isopropylthio, n-butylthio, isobutylthio, sec.-butylthio, tert.-butylthio, pentylthio, hexylthio, heptylthio, octylthio, nonylthio or decylthio; alkylthioalkyl with up to 10 and preferably 2–6 carbon atoms, for example methylthiomethyl, 2-methylthioethyl or 2-n-butylthioethyl; acylamino, preferably alkanoylamino with 1–7 and preferably 1–4 carbon atoms, such as formylamino, acetylamino, as well as propionylamino, butyrylamino, isobutyrylamino, valeroylamino, caproylamino, heptanoylamino, and also aroylamino, such as benzoylamino; acylaminoalkyl, preferably alkanoylaminoalkyl with 1–8 and preferably 3–6 carbon atoms, such as formylaminoethyl, acetylaminoethyl, propionylaminoethyl, n-butyrylaminoethyl, formylaminopropyl, acetylaminopropyl, propionylaminopropyl, formylaminobutyl, acetylaminobutyl, as well as propionylaminobutyl, butyrylaminobutyl; acyloxy with 1–6 and preferably 2–4 carbon atoms, preferably acetyloxy, propionyloxy or butyryloxy, as well as, for example, formyloxy, valeroyloxy, caproyloxy; alkoxycarbonyl with 1–5 and preferably 2 or 3 carbon atoms, preferably methoxycarbonyl or ethoxycarbonyl, as well as, for example, n-propoxycarbonyl, isopropoxycarbonyl, n-butoxycarbonyl, isobutoxycarbonyl, sec.-butoxycarbonyl or tert.-butoxycarbonyl; cycloalkoxycarbonyl with 4–8 and preferably 6 or 7 carbon atoms, preferably cyclopentyloxycarbonyl, cyclohexyloxycarbonyl, as well as cyclopropyloxycarbonyl, cyclobutyloxycarbonyl or cycloheptyloxycarbonyl; alkylaminocarbonylamino with 2–4 carbon atoms, such as methylaminocarbonylamino, ethylaminocarbonylamino, propylaminocarbonylamino; dialkylaminocarbonylamino with 3–7 and preferably 3–5 carbon atoms, preferably dimethylaminocarbonylamino, diethylaminocarbonylamino, as well as di-(n-propyl)-aminocarbonylamino, diisopropylaminocarbonylamino; (1-pyrrolidino)-carbonylamino; (1-piperidino)-carbonylamino; cycloalkylaminocarbonylamino with 4–8 and preferably 6 or 7 carbon atoms, preferably cyclopentylaminocarbonylamino, cyclohexylaminocarbonylamino, as well as cyclopropylaminocarbonylamino, cyclobutylaminocarbonylamino, cycloheptylaminocarbonylamino; alkylaminocarbonylaminoalkyl with 3–9 and preferably 4–7 carbon atoms, preferably methylaminocarbonylaminoethyl, ethylaminocarbonylaminoethyl, ethylaminocarbonylaminopropyl, ethylaminocarbonylaminobutyl, as well as, for example, methylaminocarbonylaminomethyl, n-propylaminocarbonylaminobutyl, n-butylaminocarbonylaminobutyl; dialkylaminocarbonylaminoalkyl with 4–11 carbon atoms, for example dimethylaminocarbonylaminomethyl, diethylaminocarbonylaminoethyl, diethylaminocarbonylaminopropyl, diethylaminocarbonylaminobutyl, (1-pyrrolidino)-carbonylaminoethyl, (1-piperidino)-carbonylaminoethyl; cycloalkylaminocarbonylaminoalkyl with 5–12 and preferably 8–11 carbon atoms, preferably cyclopentylaminocarbonylaminoethyl, cyclopentylaminocarbonylaminopropyl, cyclopentylaminocarbonylaminobutyl, cyclohexylaminocarbonylaminoethyl, cyclohexylaminocarbonylaminopropyl, cyclohexylaminocarbonylaminobutyl, as well as, for example, cyclopropylaminocarbonylaminomethyl, cycloheptylaminocarbonylaminoethyl; alkoxycarbonylaminoalkyl with 3–12 and preferably 4–9 carbon atoms, preferably methoxycarbonylaminoethyl, ethoxycarbonylaminoethyl, n-propoxycarbonylaminoethyl, isopropoxycarbonylaminoethyl, n-butoxycarbonylaminoethyl, isobutoxycarbonylaminoethyl, sec.-butoxycarbonylaminoethyl, tert.-butoxycarbonylaminoethyl, ethoxycarbonylaminopropyl, n-butoxycarbonylaminopropyl, ethoxycarbonylaminobutyl, n-butoxycarbonylaminobutyl, as well as, for example, n-propoxycarbonylaminopropyl, n-propoxycarbonylaminobutyl, isopropoxycarbonylaminobutyl; cycloalkoxycarbonylaminoalkyl with 5–12 and preferably 8–11 carbon atoms, preferably cyclopentyloxycarbonylaminoethyl, cyclopentyloxycarbonylaminopropyl, cyclopentyloxycarbonylaminobutyl, cyclohexyloxycarbonylaminoethyl, cyclohexyloxycarbonylaminopropyl, cyclohexyloxycarbonylaminobutyl, as well as, for example, cyclopropyloxycarbonylaminomethyl, cycloheptyloxycarbonylaminoethyl; carbamoylalkyl with 2–5 and preferably 2 carbon atoms, preferably carbamoylmethyl, as well as carbamoylethyl, carbamoylpropyl, carbamoylbutyl; alkylaminocarbonylalkyl with 3–9 and preferably 3–6 carbon atoms, preferably methylaminocarbonylmethyl, ethylaminocarbonylmethyl, n-propylaminocarbonylmethyl, isopropylaminocarbonylmethyl, n-butylaminocarbonylmethyl, isobutylaminocarbonylmethyl, sec.-butylaminocarbonylmethyl, tert.-butylaminocarbonylmethyl, as well as, for example, ethylaminocarbonylethyl, ethylaminocarbonylpropyl, ethylaminocarbonylbutyl, n-propylaminocarbonylbutyl, n-butylaminocarbonylbutyl; dialkylaminocarbonylalkyl with 4–11 and preferably 4–8 carbon atoms, preferably dimethylaminocarbonylmethyl, diethylaminocarbonylmethyl, di-(n-propyl)-aminocarbonylmethyl, (1-pyrrolidino)-carbonylmethyl, (1-piperidino)-carbonylmethyl, as well as, for example, diethylaminocarbonylethyl, (1-piperidino)-carbonylethyl, diethylaminocarbonylpropyl, diethylaminocarbonylbutyl; cycloalkylaminocarbonylalkyl with 5–12 and preferably 7 or 8 carbon atoms, preferably cyclopentylaminocarbonylmethyl, cyclohexylaminocarbonylmethyl, as well as, for example, cyclopropylaminocarbonylmethyl, cyclobutylaminocarbonylmethyl, cycloheptylaminocarbonylmethyl, cyclohexylaminocarbonylethyl, cyclohexylaminocarbonylpropyl, cyclohexylaminocarbonylbutyl; alkylaminocarbonylalkoxy with 3–10 and preferably 3–5 carbon atoms, preferably methylaminocarbonylmethoxy, as well as, for example, methylaminocarbonylethoxy, methylaminocarbonylpropoxy; dialkylaminocarbonylalkoxy with 4–10 and preferably 4–7 carbon atoms, preferably dimethylaminocarbonylmethoxy, diethylaminocarbonylethoxy, (1-piperidino)-carbonylmethoxy; cycloalkylaminocarbonylalkoxy with 5–11 and preferably 7 or 8 carbon atoms, preferably cyclopentylaminocarbonylmethoxy, cyclohexylaminocarbonylmethoxy.

Furthermore, the radical Ar can, for example, also mean 1- or 2-naphthyl; 1-, 2-, 3- (preferably) 4-, 5-, 6- or 7-indanyl; 1-oxo-4-, -5-, -6- or (preferably) -7-indanyl; alkyl-1-oxoindanyl, preferably 1-oxo-5-methyl-7-indanyl; 1-, 2-, 3-, (preferably) 4-, 5-, 6- or 7-indenyl; 1-, 2-, 3-, 4-, (preferably) 5-, 6-, 7- or 8-tetralyl; oxotetralyl, preferably 1-oxo-5-tetralyl, as well as 2-, 3- or 4-oxo-5-tetralyl or 1-, 2-, 3- or 4-oxo-6-tetralyl; (preferably) 4-, 5-, 6- or 7-indolyl; alkylindolyl, preferably methylindolyl, for example 2-methyl-4-indolyl, 3-methyl-4-indolyl or 6-methyl-4-indolyl, as well as, for example 2-ethyl-4-indolyl or 6-ethyl-4-indolyl; dialkylindolyl, preferably dimethylindolyl, for example 2,3-dimethyl-4-indolyl, 2,6-dimethyl-4-indolyl, as well as, for example, 2-methyl-3-ethyl-4-indolyl, 2-ethyl-3-methyl-4-indolyl, 2,3-diethyl-4-indolyl; cyanoinodolyl, for example 2-cyano-4-indolyl, 3-cyano-4-indolyl; alkylcycanoindolyl, preferably 2-cyano-6-methyl-4-indolyl, as well as, for example, 3-cyano-6-methyl-4-indolyl; carbamoylindolyl, preferably 2-carbamoyl-4-indolyl, 3-carbamoyl-4-indolyl, as well as, for example 6-carbamoyl-4-indolyl; alkylcarbamoylindolyl, preferably methylcarbamoylindolyl, for example 2-carbamoyl-6-methyl-4-indolyl; hydroxyalkylindolyl, preferably 2-hydroxymethyl-4-indolyl, as well as, for example, 2-hydroxymethyl-5-indolyl, 3-hydroxymethyl-4-indolyl, 2-(2-hydroxyethyl)-4-indolyl; 2-oxoindolinyl, preferably 2-oxoindolin-4-yl, as well as 2-oxoindolin-5-yl; alkyl-2-oxoindolinyl, preferably methyl-2-oxoindolin-4-yl, for example 3-methyl-2-oxoindolin-4-yl, as well as, for example, 3-ethyl-2-oxoindolin-4-yl, 3-isopropyl-2-oxoindolin-4-yl; dialkyl-2-oxoindolinyl, for example 3,3-dimethyl-2-oxoindolin-4-yl, 3,3-diethyl-2-oxoindolin-4-yl; indazol- (preferably) -4-, -5-, 6- or -7-yl; benzimidazol-4-yl; alkylbenzimidazol-4-yl, preferably methylbenzimidazol-4-yl, for example 3-methylbenzimidazol-4-yl, 1-methylbenzimidazol-4-yl, 2-methylbenzimidazol-4-yl, 6-methylbenzimidazol-4-yl, 7-methylbenzimidazol-4-yl; benzimidazolin-2-on-4-yl (preferably), benzimidazolin-2-on-5-yl; alkylbenzimidazolin-2-on-4-yl, preferably methylbenzimidazolin-2-on-4-yl, for example 6-methylbenzimidazolin-2-on-4-yl, 7-methylbenzimidazolin-2-on-4-yl; benztriazol (preferably) 4- or -5-yl; benzofuran- (preferably) 4-, -5-, -6- or -7-yl; alkylbenzofuran-4-yl, for example 2-methylbenzofuran-4-yl, 3-methylbenzofuran-4-yl, 6-methylbenzofuran-4-yl; alkanoyl-benzofuran-4-yl, for example 2-acetylbenzofuran-4-yl, 6-acetylbenzofuran-4-yl; bis-alkanoyl-benzofuran-yl, for example 2,4-diacetylbenzofuran-5-yl, 2,6-diacetylbenzofuran-4-yl; 1,3-benzodioxolyl, preferably 1,3-benzodioxol-4-yl; alkyl-1,3-benzodioxyl-4-yl, as well as, for example, 6-methyl-1,3-benzodioxol-4-yl; dialkyl-1,3-benzodioxolyl, especially 2,2-dimethyl-1,3-benzodioxol-4-yl, as well as, for example 2,2-diethyl-1,3-benzodioxol-4-yl, 2,6-dimethyl-1,3-benzodioxol-4-yl; 1,2-benzisoxazol- (preferably) 4-, -5-, -6- or -7-yl; alkyl-1,2-benzisoxazolyl, preferably 3-methyl-1,2-benzisoxazol-4-yl, as well as, for example, 3-ethyl-1,2-benzisoxazol-4-yl, 3-propyl-1,2-benzisoxazol-4-yl, 3-isopropyl-1,2-benzisoxazol-4-yl, 6-methyl-1,2-benzisoxazol-4-yl; 1,3-benzooxazol- (preferably) 4-, -5-, -6- or -7-yl; alkyl-1,3-benzoxazolyl, preferably 2-methyl-1,3-benzoxazol-4-yl, as well as, for example, 2-ethyl-1,3-benzoxazol-4-yl, 6-methyl-1,3-benzoxazol-4-yl, 6-methyl-1,3-benzoxazol-4-yl; aryl-1,3-benzoxazolyl, preferably 2-phenyl-1,3-benzoxazol-4-yl, 2-(4-pyridyl)-1,3-benzoxazol-4-yl; benzthiophen- (preferably) 4-, -5-, -6- or -7-yl; 1,2-benzisothiazol- (preferably) 4-, -5-, -6- or -7-yl; alkyl-1,2-benzisothiazol-yl, for example 6-methyl-1,2-benzisothiazol-4-yl; 1,3-benzthiazol-4-, -5-, -6- or (preferably) -7-yl; alkyl-1,3-benzthiazol-7-yl, for example 2-methyl-1,3-benzthiazol-7-yl; 4-methyl-1,3-benzthiazol-7-yl, 2-ethyl-1,3-benzthiazol-7-yl; 2-aryl-1,3-benzthiazol-7-yl, for example 2-phenyl-1,3-benzthiazol-7-yl; 2-(4-chlorophenyl)-1,3-benzthiazol-7-yl; 2-(4-pyridyl)-1,3-benzthiazol-7-yl; 1,2-dihydro-2-oxo-3-, -4- (preferably) -5-, -6-, -7- or -8-quinolyl; 1,2,3,4-tetrahydro (preferably) -5-, -6-, -7- or -8-quinolyl; 1,2,3,4-tetrahydro-2-oxo (preferably) -5-, -6-, -7- or -8-quinolyl; 1,2-dihydro-8-hydroxy-2-oxo (preferably) -5-, -6- or -7-quinolyl; 1,2-dihydro-8-alkoxy-2-oxo- (preferably) 5-, -6- or -7-quinolyl, for example 1,2-dihydro-8-methoxy-2-oxo-5-quinolyl; 1,2,3,4-tetrahydro-8-hydroxy-2-oxo- (preferably) 5-, -6- or -7-quinolyl; 1,2,3,4-tetrahydro-8-alkoxy-2-oxo- (preferably) -5-, -6- or -7-quinolyl, for example 1,2,3,4-tetrahydro-8-methoxy-2-oxo-5-quinolyl; 1,2,3,4-tetrahydro-8-alkanoylamino-2-oxo- (preferably) 5-, -6- or -7-quinolyl, for example 1,2,3,4-tetrahydro-8-acetylamino-2-oxo-5-quinolyl; 1,2-dihydro-3-cyano-2-oxo- (preferably 5-, -6-, -7- or -8-quinolyl; 1,2-dihydro-3-cyano-2-oxo-7-methyl-5-quinolyl; 1,2-dihydro-1-oxo- (preferably) 4-, -5-, -6-, -7- or -8-isoquinolyl; 1,2-dihydro-2-alkyl-1-oxo- (preferably) 4-, -5-, -6-, -7- or -8-isoquinolyl, for example 1,2-dihydro-2-methyl-1-oxo-4-isoquinolyl; 1,2,3,4-tetrahydro-2-alkanoyl- (preferably) 5-, -6-, -7- or -8-isoquinolyl, preferably 1,2,3,4-tetrahydro-2-formyl-5-isoquinolyl, as well as, for example, 1,2,3,4-tetrahydro-2-acetyl-5-isoquinolyl; 1,2-dihydro-2-oxo-1,3-benzodiazin- (preferably) 5-, -6-, -7- or -8-yl; 2H-3,4-dihydro-5-, -6-, -7- or (preferably)- 8-benzopyranyl; 2H-2-oxo-5-alkyl-7- or (preferably) 8-benzopyranyl, for example 2H-2-oxo-5-methyl-8-benzopyranyl; 2H-3-cyano-5-, -6-, -7- or (preferably) -8-benzopyranyl; 2H-3,4-dihydro-5-, -6-, -7- or (preferably) -8-benzothiinyl, 3,4-dihydro1H-2,2-dioxo-2,1-benzothiazin- (preferably) 5-, -6-, -7- or -8-yl; 3,4-dihydro-1H-1-alkyl-2,2-dioxo-2,1-benzothiazin- (preferably) 5-, -6-, -7- or -8-yl, for example 3,4-dihydro-1H-1-methyl-2,2-dioxo-2,1-benzothiazin-5-yl; 3,4-dihydro-2H-3-oxo-1,4-benzothiazin-5-, -6-, -7- or (preferably -8-yl; 5- or 6-alkyl-3,4-dihydro-2H-3-oxo-1,4-benzothiazin-8-yl, for example 6-methyl-3,4-dihydro-3-oxo-1,4-benzothiazin-8-yl; 1,1-dioxo-1,2,4-benzothiazin-5-, -6-, -7- or -8-yl; 1,1-dioxo-3-alkyl-1,2,4-benzothiadiazin-5-, -6-, -7- or -8-yl, for example 1,1-dioxo-3-methyl-1,2,4-benzothiadiazin-5-, -6-, -7- or -8-yl; 1,1-dioxo-3-alkanoyl-1,2,4-benzothiadiazin-5-, -6-, -7- or -8-yl, for example 1,1-dioxo-3-formyl-1,2,4-benzothiadiazin-5-, -6-, -7- or -8-yl, 1,1-dioxo-3-acetyl-1,2,4-benzothiadiazin-5-, -6-, -7- or -8-yl; 1,1-dioxo-3-aroyl-1,2,4-benzothiadiazin-5-, -6-, -7- or -8-yl, for example 1,1-dioxo-3-benzoyl-1,2,4-benzothiadiazin-5-, -6-, -7- or -8-yl, 1,1-dioxo-3-(4-pyridylcarbonyl)-1,2,4-benzothiadiazin-5-, -6-, -7- or -8-yl; 3,4-dihydro-2,2-dioxo-1,2-benzooxathiin- (preferably) 5-, -6-, -7- or (preferably) -8-yl; 1-, 2-, 3- or (preferably) 4-carbazolyl.

A can be a straight-chained alkylene chain of 1–8 and preferably 2–4 carbon atoms, preferably ethylene, trimethylene, tetramethylene, as well as methylene, pentamethylene, hexamethylene or heptamethylene, octamethylene. The alkylene chain can also be branched and consist of 3–8 and preferably 3–6 carbon atoms. There are preferred, for example, propylene, 1,1-dimethylethylene, 1-methyltrimethylene, 1,1-dimethyltrimethylene, 2,2-dimethyltrimethylene and 1-methyltetramethylene. There may also be mentioned, for example, 1-ethyltrimethylene, 1,1-dimethyltetramethylene, 1,2-dimethyltetramethylene, 2,2-dimethyltetramethylene, 2,3-dimethyltetramethylene, 3,3-dimethylpentamethylene, 1-methylhexamethylene and 1-methylheptamethylene. A —CH$_2$— group or an alkylene chain can be replaced by a cycloalkylene radical with 3–7 and preferably 6 carbon atoms. A 1,2-, 1,3- or 1,4-cyclohexylene radical is preferred in which the position of the substituents can be cis or trans. Furthermore, there can be introduced, for example, a methylene-1,2-, -1,3- or -1,4-cyclohexylene radical, a methylene-1,2-, -1,3- or -1,4-cyclohexylenemethylene radical, an ethylene-1,2-, -1,3- or -1,4-cyclohexylene radical, a trimethylene-1,1-, -1,3- or -1,4-cyclohexylene radical, a tetramethylene-1,2-, -1,3- or -1,4-cyclohexylene radical or also a methylene-1,2-, -1,3- or -1,4-cyclohexyleneethylene radical or an ethylene-1,2-, -1,3- or -1,4-cyclohexylenetetramethylene radical, and the configuration of the cycloalkylene radical can be cis or trans. Furthermore, the alkylene chain can be, for example, a 1,2-cyclopropylene radical, a methylene-1,2-cyclopropylene radical, a tetramethylene 1,2-cyclopropylene radical, a methylene-1,2-cyclopropylenemethylene radical, a methylene-1,2-cyclopropyleneethylene radical, a 1,2- or 1,3-cyclobutylene radical, a methylene-1,2- or -1,3-cyclobutylene radical, a tetramethylene-1,2- or 1,3-cyclopbutylene radical, a methylene-1,2- or -1,3- cyclobutylenemethylene radical, a methylene-1,2- or -1,3 cyclobutyleneethylene radical, a 1,2- or 1,3-cyclopentylene radical, a methylene-1,2- or -1,3-cyclopentylene radical, a tetramethylene-1,2- or -1,3-cyclopentylene radical, a methylene-1,2- or -1,3-cyclopentylenemethylene radical, a methylene-1,2- or -1,3-cyclopentylene-ethylene radical, a 1,2-, 1,3- or 1,4-cycloheptylene radical, a methylene-1,2-, -1,3- or 1,4-cycloheptylene radical, a tetramethylene-1,2-, -1,3- or -1,4-cycloheptylene radical, a methylene-1,2-, -1,3- or -1,4-cycloheptylenemethylene radical or a methylene-1,2-, -1,3- or -1,4-cycloheptylene-ethylene radical, the configuration of the cycloalkylene radical being cis or trans.

The group B can be a straight-chained or branched alkylene chain with 1–12 and preferably 4–6 carbon atoms and is preferably tetramethylene, 1-methyltrimethylene, pentamethylene, 1-methyltetramethylene, 1-ethyltrimethylene, hexamethylene, 1-methylpentamethylene, 1-ethyltetramethylene, 1-n-propyltrimethylene or 1,1-dimethylethylene, as well as, for example, methylene, methylmethylene, dimethylmethylene, 2,2-dimethyltrimethylene, 1,1-dimethylhexamethylene, whereby in all cases 1 or 2 hydrogen atoms can be replaced by an —O—NO$_2$— group. Preferred cyclic and bicyclic alkylene chains B include the 1,2-cyclopentylene radical, the 1,2-, 1,3- or 1,4-cyclohexylene group, the 1,2-cyclohexylenemethylene or the 2,5-isosorbide radical, whereby the configuration of the cycloalkylene radical can be cis or trans, as well as, for example, the 1,2-, 1,3- or 1,4-phenylenemethylene radical, the methylene-1,2-, -1,3- or -1,4-phenylenemethylene radical, the ethylene-1,4-phenylene radical, the ethylene-1,4-phenyleneethylene radical, the ethylene-1,4-phenylenetetramethylene radical or the trimethylene-1,4-phenylenetrimethylene radical, whereby in all cases 1 or 2 hydrogen atoms can be replaced by the —O—NO$_2$ group.

When X represents the group —NR$^1$—, R$^1$ can be a hydrogen atom or a straight-chained or branched, saturated or unsaturated alkyl radical containing up to 6 and preferably up to 3 carbon atoms, preferably a methyl, ethyl, n-propyl, isopropyl or allyl radical, as well as, for example, an n-butyl, n-pentyl or n-hexyl radical. When R$^1$, together with a —CH$_2$— group of the chain B and the nitrogen atom form a heteroaliphatic ring with 4 to 6 carbon atoms, then this is preferably a pyrrolidinylene, piperidinylene or 1,2-, 1,3- or 1,4-piperidinylene- methylene radical, as well as, for example, a perhydroazepinylene radical.

Compounds of a similar kind have already been described, for example, in Federal Republic of Germany Patent Specification No. 2,362,568, European Patent Specifications Nos. 0,082,665, 0,086,564, 0,096,006 and 0,105,838, British Patent Specification No. 2,111,500 and PCT Patent Specifications Nos. WO 83/01770 and WO 83/01772. However, the compounds described therein differ from the compounds according to the present invention in that they do not contain the grouping —O—NO$_2$.

The new compounds according to the present invention of general formula (I) possess valuable properties. They not only have a β-receptor-blocking activity but they also bring about a reduction of the oxygen requirement of the heart, an increase of the blood flow and a lowering of the blood pressure. Therefore, they can be used for the prophylaxis and/or treatment of heart and circulatory diseases, for example high pressure and angina pectoris.

The compounds according to the present invention are usually administered in amounts of from 20 to 500 mg, per day, referred to a body weight of 75 kg. It is preferred to administer, 2 or 3 times a day, 1 to 2 tablets with a content of active material of 10 to 200 mg. The tablets can also be retarded, in which case only 1 to 2 tablets with 20 to 500 mg. of active material have to be given once per day. The active material can also be administered by injection 1 to 8 times a day or by continuous infusion, in which case amounts of from 5 to 200 mg./day normally suffice.

The compounds of general formula (I) according to the present invention can be prepared in per se known manner in that:

(a) a compound of the general formula:

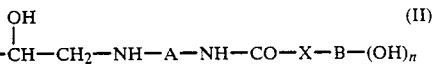

Ar—O—CH$_2$—CH(OH)—CH$_2$—NH—A—NH—CO—X—B—(OH)$_n$     (II)

in which A, Ar, B, X and n have the above-given meanings, is subjected to a nitrate ester-formation reaction; or (b) a compound of the general formula:

Ar'—O—Z     (III)

in which Ar' has the same meaning as Ar or is optionally a corresponding synthesis precursor and Z is a radical of the formula:

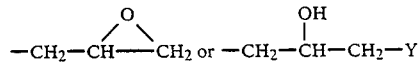

in which Y is a reactive group, is reacted (b 1) with an amine of the general formula:

H$_2$N—A—NH—CO—X—B—(ONO$_2$)$_n$     (IV)

in which A, B, X and n have the above-given meanings or (b 2) with an amine of the general formula:

H$_2$N—A—(NH$_2$)$_{mask.}$     (V), in which A has the above-given meaning and —(NH$_2$-)$_{mask.}$ is a free —NH$_2$ group or a masked —NH$_2$ group, to give a compound of the general formula:

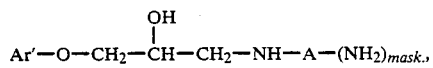

$$\text{Ar}'\text{—O—CH}_2\text{—CH(OH)—CH}_2\text{—NH—A—(NH}_2)_{mask},\quad\text{(VI)}$$

and this, possibly after demasking the —(NH$_2$)$_{mask.}$ grouping to give an —NH$_2$ group and/or after conversion of the Ar' group into an Ar group, is reacted with a compound of the general formula:

$$\text{Y—CO—X—B—(ONO}_2)_n\quad\text{(VII)},$$

in which B, X, Y and n have the above-given meanings; or (c) a compound of the general formula:

$$\text{Ar}'\text{—OH}\quad\text{(VIII)},$$

in which Ar' has the above-given meaning, is reacted (c 1) with a compound of the general formula:

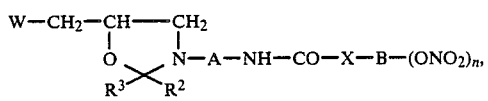

(IX)

in which A, B, X and n have the above-given meanings, W is a mesyloxy or tosyloxy radical or a halogen atom, R$^3$ is a hydrogen atom or an alkyl radical and R$^2$ independently represents a hydrogen atom or an alkyl or phenyl radical or R$^2$ and R$^3$, together with the neighbouring carbon atom, form a carbonyl radical, and the Ar' group is possibly converted into an Ar group and the oxazolidine ring is split; or (c 2) with a compound of the general formula:

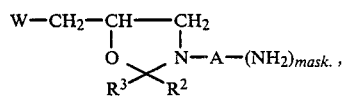

(X)

in which A, R$^2$, R$^3$, W and —(NH$_2$)$_{mask.}$ have the above-given meanings, the oxazolidine ring is split and the compound obtained for general formula (VI), possibly after conversion of the Ar' group in the Ar group and/or after demasking of the —(NH$_2$)$_{mask.}$ group to give an —NH$_2$ group, is reacted with a compound of the general formula (VII); or (c 3) with a compound of the general formula:

(XI)

in which A, B, W, X and n have the above-given meanings, and possibly the group Ar' is converted into an Ar group; or (c 4) with a compound of the general formula:

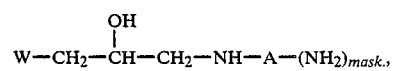

(XII)

in which A, W and —(NH$_2$)$_{mask.}$ have the above-given meanings, to give a compound of general formula (VI) and this, possibly after conversion of the Ar' group into an Ar group and/or after demasking of the group —(NH$_2$)$_{mask.}$ to give an —NH$_2$ group, reacted with a compound of the general formula (VII); or (d) a compound of the general formula:

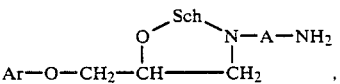

(XIII)

in which A and Ar have the above-given meanings and Sch is a dialkylsilylene radical, is reacted with a compound of general formula (VII) and the Sch grouping is split off.

The compounds of general formula (II) (intermediates for the preparation of compounds of general formula (I) are also new and the subject of the present invention. They can be prepared in that, in known manner, (a) a compound of general formula (III) is reacted (a 1) with an amine of the general formula:

$$\text{H}_2\text{N—A—NH—CO—X—B—(OH)}_n\quad\text{(XIV)},$$

in which A, B, X and n have the above-given meanings: or (a 2) with an amine of general formula (V) to give a compound of general formula (VI) and this, possibly after demasking the —(NH$_2$)$_{mask.}$ group to give an —NH$_2$ group and/or conversion of the Ar' group into the Ar group, reacted with a compound of the general formula:

$$\text{Y—CO—X—B—(OH)}_n\quad\text{(XV)},$$

in which B, X, Y and n have the above-given meanings; or (b) a compound of the general formula (VIII) is reacted (b 1) with a compound of the general formula:

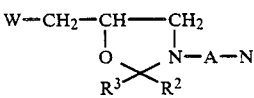

(XVI)

in which A, B, R$^2$, R$^3$, W, X and n have the above-given meanings, and the oxazolidine ring is split; or (b 2) with a compound of general formula (X), the oxazolidine ring is split and the compound so obtained of general formula (VI), possibly after conversion of the Ar' group into an Ar group and/or after demasking of the —(NH$_2$)$_{msk.}$ group to give an —NH$_2$ group, is reacted with a compound of general formula (XV); or (b 3) with a compound of the general formula:

(XVII)

in which A, B, W, X and n have the above-given meanings, and the Ar' group possibly converted into an Ar group; or (b 4) with a compound of general formula (XII), to give a compound of general formula (VI) and this, possibly after conversion of the Ar' group into an Ar group and/or after demasking of the —(NH$_2$)$_{mask.}$ group to give an —NH$_2$ group, reacted with a compound of general formula (XV); or (c) a compound of general formula (XIII) is reacted with a compound of general formula (XV) and the Sch group is split off.

The amines of general formula (IV) can be prepared in per se known manner in that:

(a) a compound of the general formula:

$$\text{H}_2\text{N—A—NH}_2\quad\text{(XVIII)}$$

in which A has the above-given meaning, is reacted with an activated compound of general formula (VII); or (b) a compound of general formula (XVIII) is reacted with an activated compound of general formula (XIV) to give a compound of general formula (XV) and this is subjected to a nitrate ester-formation reaction; or (c) a masked compound of general formula (V) is reacted with an activated compound of general formula (VII) and the —(NH$_2$)$_{mask.}$ group is demasked to give an —NH$_2$ group; or (d) a compound of general formula (V) is reacted with an activated compound of general formula (XV) and, after demasking of the —(NH$_2$)$_{mask.}$ group to give an —NH$_2$ group, the compound obtained of general formula (XIV) is subjected to a nitrate ester-formation reaction.

The nitrate ester-formation reaction of compounds of general formulae (II) and (XIV) can be carried out by reacting a compound of general formula (II) or (XIV) with a nitrate ester-forming reagent, such as fuming nitric acid, a mixture of fuming nitric acid and acetic anhydride or a mixture of fuming nitric acid and concentrated sulphuric acid, at a low temperature in the presence or absence of an inert solvent. The reaction temperature is from ambient temperature to −60° C., and preferably from −10° C. to −30° C. The mole ratio of the reaction components is from 1 to 10.

Alternatively, the nitrate ester-forming reaction can be carried out by selectively replacing an aliphatic hydroxyl group in a compound of general formula (II) or (XIV) by a halogen atom and subsequently reacting the reaction product with silver nitrate in the presence or absence of a solvent at a temperature of from ambient temperature to 100° C. The mole ratio of the components of the reaction between the halogen compound and silver nitrate can be from 1 to 10.

The halogenation reaction can be carried out according to processes known from the literature by reacting a compound of general formula (II) or (XIV) with mesyl chloride or tosyl chloride in the presence of an acid-binding agent, the reaction product obtained being substantially reacted with an alkali metal halide in an organic solvent, for example dimethylformamide.

The reactions of compounds of general formula (VIII) with epihalohydrins or compounds of general formulae (IX), (X), (XI), (XII), (XVI) and (XVII) are carried out in per se known manner by reacting the reaction components in an organic solvent and/or water in the presence of an acid-binding agent, for example an alkali metal hydroxide or hydride or an organic nitrogen base, at a temperature of from ambient temperature to 100° C. The mole ratio of the compounds of general formula (VIII) to the epihalohydrins or to the compounds of general formulae (IX), (X), (XI), (XII), (XVI) and (XVII) can be from 1 to 100. As organic solvents, there can be used, for example, methanol, ethanol, propanol, benzene, toluene, tetrahydrofuran, dimethylformamide or dimethyl sulphoxide. The splitting of the oxazolidine rings in compounds of general formulae (IX) and (X) takes place under acidic conditions when R$^2$ and R$^3$ are hydrogen atoms or alkyl or aryl radicals or under basic conditions, for example in 4N aqueous sodium hydroxide solution/ethanol, when R$^2$ and

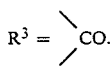

The reaction of a compound of general formula (III) with an amine of general formula (IV), (V) or (XIV) takes place in the presence or absence of a solvent at a temperature of from 0° to 150° C. and preferably of from 20° to 50° C. As solvent, there can be used, for example, methanol, ethanol, propanol, isopropanol, benzene, toluene or dimethylformamide. The mole ratio of the reaction components is not critical and there can be used ratios of from 1 to 100.

A masked —(NH$_2$)$_{mask.}$ group in compounds of general formulae (V), (VI), (X) and (XII) can be, for example, an acylated, preferably acetylated, —NH—acyl radical, an —NH—C$_7$H$_7$ or —N(C$_7$H$_7$)$_2$ radical protected by 1 or 2 benzyl radicals or a nitro group —NO$_2$ or, together with the neighbouring carbon atom, can also form a —CN group. The demasking of the —NH—acyl radical preferably takes place with an inorganic acid or base, for example hydrochloric acid or aqueous sodium hydroxide solution, in the presence or absence of an organic solvent, for example methanol or ethanol, at a temperature of from ambient temperature to 150° C., the mole ratio being from 1 to 200. The splitting off of a benzyl protective group takes place hydrogenolytically in the presence of an organic solvent and/or water, as well as of palladium-on-charcoal as catalyst. The temperature used can be from ambient temperature to 250° C. and is preferably of from ambient temperature to 60° C. and the hydrogen pressure used can be from 1 to 300 bar and is preferably from 1 to 5 bar. For the reduction of the —NO$_2$ group, there can be used numerous processes, for example with zinc in hydrochloric acid, with iron in hydrochloric acid, with lithium aluminium hydride in an ether, with an inorganic sulphide, for example, sodium hydrogen sulphide, ammonium sulphide or sodium dithionite, in aqueous and/or alcoholic solution, or hydrogenolytically with a catalyst, such as platinum oxide, palladium or Raney nickel, preferably in an alcoholic solvent, such as methanol or ethanol, at a pressure of from 1 to 200 bar. The temperature used can be from −20° C. to +200° C. and is preferably from ambient temperature to 100° C. The reduction of a —CN group to a —CH$_2$—NH$_2$ radical can take place, for example, with lithium aluminium hydride in an ether, diborane in an ether or hydrogenolytically with a catalyst, such as Raney nickel or platinum oxide, in an organic solvent and/or water at a pressure of from 1 to 300 bar. The temperature used can be from −30° C. to +200° C.

The reaction of amines of the general formula (V), (XIII) and (XVIII) or of demasked amines (—(NH$_2$.)$_{mask.}$=NH$_2$) (VI) with activated compounds of general formulae (VII) or (XV) is carried out in an organic solvent, for example hexane, diethyl ether, tetrahydrofuran, methylene chloride, benzene, toluene or dimethylformamide, or in aqueous solution at a temperature of from −50° C. to +100° C. and preferably of from −30° C. and ambient temperature.

When
(a) X=valency bond the corresponding activated carboxylic acids can be present, for example, in the form of esters, lactones, carboxylic acid halides or anhydrides or the activation of the carboxylic acids can take place by activating reagents, for example N,N'-carbonyldiimidazole, N,N'-dicyclohexylcarbodiimide, 1-ethyl-3-(3-dimethylaminopropyl)-carbodiimide, a 1-alkyl-2-halopyridinium salt or the like. The activation and the reaction with the amines of general formulae (V), (XIII) and (XVIII) or with the demasked amines of general formula (VI) can thereby be carried out in one synthesis step. There can be used mole ratios of from 1 to 10. The reactions can possibly be carried out in the presence of an adjuvant base, preferably an organic amine.

(b) X=an oxygen atom corresponding alcohols can be reacted with carbonyl-forming reagents, such as phosgene, chloroformic acid esters, carbonic acid diesters, N,N'-carbonyldiimidazole and the like and the intermediates obtained reacted with amines of general formulae (V), (XIII) and (XVIII) or demasked amines (—$NH_2$)$_{mask.}$=—$NH_2$) (VI). The attachment of the alcohols and of the corresponding amines to the urethanes can thereby be carried out in a one-pot process. An adjuvant base, preferably an organic amine, can possibly be added. The mole ratios between the alcohols and the carbonyl-forming reagents, on the one hand, and the amines of general formulae (V), (XIII) and (XVIII) or the demasked amines of general formula (VI), on the other hand, can be from 1 to 10 and preferably 1.

(c) X=—$NR^1$ corresponding amines can be reacted with carbonyl-forming reagents, such as phosgene, urea, chloroformic acid esters, carbonic acid diesters, N,N'-carbonyldiimidazole and the like, and the intermediates obtained reacted with the amines of general formulae (V), (XIII) and (XVIII) or the demasked amines (—$NH_2$)$_{mask.}$=—$NH_2$). The urea formation can also be carried out in a one-pot process. An adjuvant base, preferably an organic amine, can be added. Instead of an amine and of the carbonyl-forming reagent, there can also be used corresponding isocyanates of the general formulae O=C=N—B—(ONO$_2$)$_n$ and O=C=N—B—(OH)$_n$, in which B and n have the above-given meanings. The mole ratio between the isocyanates or the corresponding amines and the carbonyl-forming reagents, on the one hand, and the amines of general formulae (V), (XIII) and (XVIII) or the demasked amines (—$NH_2$)$_{mask.}$=—$NH_2$) (VI), on the other hand, can be from 1 to 10 and is preferably 1.

For the preparation of compounds of general formula (XIII), compounds of the general formula (VI) (—$NH_2$)$_{mask.}$=—$NH_2$) are reacted with bifunctional silicon compounds, for example dimethyldichlorosilane, bis-(acetyloxy)-dimethylsilane, bis-(N-acetyl-N-methylamino)-dimethylsilane, bis-(dimethylamino)-dimethylsilane, bis-(1,3-imidazol-1-yl)-dimethylsilane or 1,3-dichloro-1,1,3,3-tetraisopropyldisiloxane, in an organic solvent, for example diethyl ether, tetrahydrofuran, 1,4-dioxan, benzene, toluene or dimethylformamide, in the presence of an organic base, for example triethylamine or imidazole. The temperature is from −30° to +100° C. and preferably from ambient temperature to 100° C. The mole ratio can be from 1 to 10. After the possibly necessary conversion of the Ar' group into the Ar group, the compound obtained of general formula (XIII) is reacted with an activated compound of general formula (VII) or (XV) and the protective group Sch is split off by the addition of an alcohol, for example methanol or isopropanol, or of a fluoride salt, for example sodium fluoride, tetra-n-butylammonium fluoride or the like, in an organic solvent, for example tetrahydrofuran or diethyl ether. The splitting off of the protective group Sch can also take place with aqueous ammonia solution or with acid/water mixtures, for example acetic acid/water (2:1 v/v) or hydrogenolytically over palladium-on-charcoal. The temperatures used are from −20° to +150° C. and preferably from 0° C. to ambient temperature. The mole ratios can be from 1 to 100.

The compounds according to the present invention of general formulae (I), (II), (III), (VI), (IX), (X), (XI), (XII), (XIII), (XVI) and (XVII) possess asymmetric carbon atoms. Therefore, the present invention also provides all possible diastereomeric mixtures, racemates and all optically-active forms of the compounds of general formulae (I), (II), (IX), (X), (XVI) and (XVII).

For the conversion of compounds of general formulae (I) and (II) into their pharmacologically acceptable salts, they are reacted, preferably in an organic solvent, with the equivalent amount of an inorganic or organic acid, for example hydrochloric acid, hydrobromic acid, nitric acid, phosphoric acid, sulphuric acid, formic acid, acetic acid, propionic acid, oxalic acid, fumaric acid, maleic acid, succinic acid, adipic acid, benzoic acid, salicylic acid, o-acetoxybenzoic acid, cinnamic acid, naphthoic acid, mandelic acid, citric acid, malic acid, tartaric acid, aspartic acid, glutamic acid, methanesulphonic acid or p-toluenesulphonic acid.

The new compounds of general formulae (I) and (II) according to the present invention can be administered enterally or parenterally in liquid or solid form. As injection medium, it is preferable to use water which contains the additives usual in the case of injection solutions, such as stabilising agents, solubilising agents or buffers. Such additives include, for example, tartrate and citrate buffers, ethanol, complex formers (such as ethylenediamine-tetraacetic acid and the non-toxic salts thereof) and high molecular weight polymers (such as liquid polyethylene oxide) for viscosity regulation. Solid carrier materials include, for example, starch, lactose, mannitol, methyl cellulose, talc, highly dispersed silicic acids, high molecular weight fatty acids (such as stearic acid), gelatine, agar-agar, calcium phosphate, magnesium stearate, animal and vegetable fats and solid high molecular weight polymers (for example polyethylene glycols). Compositions suitable for oral administration can, if desired, contain flavouring and sweetening agents.

Besides the compounds described in the following Examples, preferred compounds according to the present invention include the following:

1-(1-naphthyloxy)-3-[2-(3-nitroxybutanoylamino)-ethylamino]-propan-2-ol
1-(2-methylindol-4-yloxy)-3-[2-(3-nitroxybutanoylamino)ethylamino]-propan-2-ol
1-(2-allylphenoxy)-3-[2-(2,2-dimethyl-3-nitroxypropanoylamino)-ethylamino]-propan-2-ol
3-[2-(2,2-dimethyl-3-nitroxypropanoylamino)-ethylamino]-1-(indol-4-yloxy)-propan-2-ol
3-[2-(2,2-dimethyl-3-nitroxypropanoylamino)-ethylamino]-1-(2-methylindol-4-yloxy)-propan-2-ol
1-(4-carbamoylmethylphenoxy)-3-[2-(4-nitroxybutanoylamino)-ethylamino]-propan-2-ol
1-(4-hydroxy-2,3,5-trimethylphenoxy)-3-[2-(4-nitroxybutanoylamino)-ethylamino]-propan-2-ol
3-[1,1-dimethyl-2-(4-nitroxybutanoylamino)-ethylamino]-1-(2-methylindol-4-yloxy)-propan-2-ol 3-[1,1-dimethyl-2-(4-nitroxybutanoylamino)-ethylamino]-1-(6-methylindol-4-yloxy)-propan-2-ol 1-(2-cyanoindol-4-yloxy)-3-[1,1-dimethyl-2-(4-nitroxybutanoylamino)-ethylamino]-propan-2-ol 1-(1-naphthyloxy)-3-[2-(4-nitroxypentanoylamino)ethylamino]-propan-2-ol 1-(2-methylindol-4-yloxy)-3-[2-(4-nitroxypentanoylamino)-ethylamino]-propan-2-ol 1-(1,2,3,4-tetrahydro-7-methyl-2-oxoquinolin-5-yloxy)-3-[2-(4-nitroxypentanoylamino)-ethylamino]-propan-2-ol 1-(2-allylphenoxy)-3-[2-(5-nitroxypentanoylamino)ethylamino]-propan-2-ol 1-[4-(2-methoxyethyl)-phenoxy]-3-[2-(5-nitroxypentanoylamino)-ethylamino]-propan-2-ol 1-(2-cyclopentylphenoxy)-3-[2-(5-nitroxypentanoylamino)ethylamino]-propan-2-ol 1-(2-allyloxyphenoxy)-3-[2-(5-nitroxypentanoylamino)ethylamino]-propan-2-ol 1-(4-methylcarbonyloxy-2,3,5-trimethylphenoxy)-3-[2-(5-nitroxypentanoylamino)-ethylamino]-propan-2-ol 1-(4-hydroxy-2,3,5-trimethylphenoxy)-3-[2-(5-nitroxypentanoylamino)-ethylamino]-propan-2-ol 1-(3-cyano-6-methylindol-4-yloxy)-3-[2-(5-nitroxypentanoylamino)-ethylamino]-propan-2-ol 1-(1,2-dihydro-2-oxoquinolin-5-yloxy)-3-[2-(5-nitroxypentanoylamino)-ethylamino]-propan-2-ol 1-(1,2-dihydro-7-methyl-2-oxoquinolin-5-yloxy)-3-[2-(5-nitroxypentanoylamino)-ethylamino]-propan-2-ol 1-(2,6-dimethylindol-4-yloxy)-3-[2-(5-nitroxypentanoylamino)-ethylamino]-propan-2-ol 1-(2-allylphenoxy)-3-[2-[(t-3,c-4-dinitroxycyclohexyl)-r-1-carbonylamino]-ethylamino]-propan-2-ol 1-(2-cyanophenoxy)-3-[2-[(t-3,c-4-dinitroxycyclohexyl)-r-1-carbonylamino]-ethylamino]-propan-2-ol 3-[2-[(t-3,c-4-dinitroxycyclohexyl)-r-1-carbonylamino]ethylamino]-1-(indol-4-yloxy)-propan-2-ol 3-[2-[(t-3,c-4-dinitroxycyclohexyl)-r-1-carbonylamino]ethylamino]-1-(2-methylindol-4-yloxy)-propan-2-ol trans-1-[4-(n-butanoylamino)-2-methylcarbonylphenoxy]-3-[2-[(2-nitroxycyclohexyl)-acetylamino]-ethylamino]-propan-2-ol trans-1-(2-methylindol-4-yloxy)-3-[2-[(2-nitroxycyclohexyl)-acetylamino]-ethylamino]-propan-2-ol trans-1-(6-methylindol-4-yloxy)-3-[2-[(2-nitroxycyclohexyl)-acetylamino]-ethylamino]-propan-2-ol trans-1-(3-cyano-6-methylindol-4-yloxy)-3-[2-[(2-nitroxycyclohexyl)-acetylamino]-ethylamino]-propan-2-ol trans-1-(1,2,3,4-tetrahydro-7-methyl-2-oxoquinolin-5-yloxy)-3-[2-[(2-nitroxycyclohexyl)-acetylamino]ethylamino]-propan-2-ol trans-1-(carbazol-4-yloxy)-3-[2-[(2-nitroxycyclohexyl)acetylamino]-ethylamino]-propan-2-ol 1-(2-chloro-5-methylphenoxy)-3-[2-(2-methyl-4-nitroxybutanoylamino)-ethylamino]-propan-2-ol 1-(4-methylcarbonyloxy-2,3,5-trimethylphenoxy)-3-[2-(2-methyl-4-nitroxybutanoylamino)-ethylamino]-propan-2-ol 1-(4-hydroxy-2,3,5-trimethylphenoxy)-3-[2-(2-methyl-4-nitroxybutanoylamino)-ethylamino]-propan-2-ol 1-(6-methylindol-4-yloxy)-3-[2-(2-methyl-4-nitroxybutanoylamino)-ethylamino]-propan-2-ol 1-(1,2,3,4-tetrahydro-2-oxoquinolin-5-yloxy)-3-[2-(2-methyl-4-nitroxybutanoylamino)-ethylamino]-propan-2-ol 1-(2-methylindol-4-yloxy)-3-[2-(5-nitroxyhexanoylamino)ethylamino]-propan-2-ol 1-[4-(2-methoxyethyl)-phenoxy]-3-[2-[(2-nitroxyethoxy)acetylamino]-ethylamino]-propan-2-ol 1-(2-cyclopentylphenoxy)-3-[2-[(2-nitroxyethoxy)acetylamino]-ethylamino]-propan-2-ol 1-(2-cyanophenoxy)-3-[2-[(2-nitroxyethoxy)-acetylamino]ethylamino]-propan-2-ol 1-(2-chloro-5-methylphenoxy)-3-[2-[(2-nitroxyethoxy)acetylamino]-ethylamino]-propan-2-ol 1-(4-methylcarbonyloxy-2,3,5-trimethylphenoxy)-3-[2-[(2-nitroxyethoxy)-acetylamino]-ethylamino]-propan-2-ol 1-(4-hydroxy-2,3,5-trimethylphenoxy)-3-[2-[(2-nitroxyethoxy)-acetylamino]-ethylamino]-propan-2-ol 1-(1-naphthyloxy)-3-[2-[(2-nitroxyethoxy)-acetylamino]ethylamino]-propan-2-ol 1-(indol-4-yloxy)-3-[2-[(2-nitroxyethoxy)-acetylamino]ethylamino]-propan-2-ol 1-(2-methylindol-4-yloxy)-3-[2-[(2-nitroxyethoxy)acetylamino]-ethylamino]-propan-2-ol 1-(6-methylindol-4-yloxy)-3-[2-[(2-nitroxyethoxy)acetylamino]-ethylamino]-propan-2-ol 1-(2-cyanoindol-4-yloxy)-3-[2-[(2-nitroxyethoxy)acetylamino]-ethylamino]-propan-2-ol 1-(3-cyano-6-methylindol-4-yloxy)-3-[2-[(2-nitroxyethoxy)-acetylamino]-ethylamino]-propan-2-ol 3-[2-[(2-nitroxyethoxy)-acetylamino]-ethylamino]-1-(2-oxoindolin-4-yloxy)-propan-2-ol 1-(1,2,3,4-tetrahydro-2-oxoquinolin-5-yloxy)-3-[2-[(2-nitroxyethoxy)-acetylamino]-ethylamino]-propan-2-ol 1-(1,2-dihydro-2-oxoquinolin-5-yloxy)-3-[2-[(2-nitroxyethoxy)-acetylamino]-ethylamino]-propan-2-ol 1-(3-methylbenzimidazol-4-yloxy)-3-[2-[(2-nitroxyethoxy)-acetylamino]-ethylamino]-propan-2-ol 1-(2,6-dimethylindol-4-yloxy)-3-[2-[(2-nitroxyethoxy)acetylamino]-ethylamino]-propan-2-ol 1-(2-allylphenoxy)-3-[2-[(2-nitroxyethylthio)-acetylamino]-ethylamino]-propan-2-ol 1-[4-(2-methoxyethyl)-phenoxy]-3-[2-[(2-nitroxyethylthio)-acetylamino]-ethylamino]-propan-2-ol 1-(2-cyclopentylphenoxy)-3-[2-[(2-nitroxyethylthio)acetylamino]-ethylamino]-propan-2-ol 1-(2-cyanophenoxy)-3-[2-[(2-nitroxyethylthio)acetylamino]-ethylamino]-propan-2-ol 1-(4-methylcarbonyloxy-2,3,5-trimethylphenoxy)-3-[2-[(2-nitroxyethylthio)-acetylamino]-ethylamino]-propan-2-ol 1-(4-hydroxy-2,3,5-trimethylphenoxy)-3-[2-[(2-nitroxyethylthio)-acetylamino]-ethylamino]-propan-2-ol 1-(1-naphthyloxy)-3-[2-[(2-nitroxyethylthio)-acetylamino]-ethylamino]-propan-2-ol 1-(indol-4-yloxy)-3-[2-[(2-nitroxyethylthio)-acetylamino]-ethylamino]-propan-2-ol 1-(6-methylindol-4-yloxy)-3-[2-[(2-nitroxyethylthio)acetylamino]-ethylamino]-propan-2-ol 1-(2-cyanoindol-4-yloxy)-3-[2-[(2-nitroxyethylthio)acetylamino]-ethylamino]-propan-2-ol 1-(3-cyanoindol-4-yloxy)-3-[2-[(2-nitroxyethylthio)acetylamino]-ethylamino]-propan-2-ol 1-(3-cyano-6-methylindol-4-yloxy)-3-[2-[(2-nitroxyethylthio)-acetylamino]-ethylamino]-propan-2-ol 3-[2-[(2-nitroxyethylthio)-acetylamino]-ethylamino]-1-(2-oxoindolin-4-yloxy)-propan-2-ol 1-(1,2,3,4-tetrahydro-2-oxoquinolin-5-yloxy)-3-[2-[(2-nitroxyethylthio)-acetylamino]-ethylamino]-propan-2-ol 1-(1,2-dihydro-2-oxoquinolin-5-yloxy)-3-[2-[(2-nitroxyethylthio)-acetylamino]-ethylamino]-propan-2-ol 1-(1,2-dihydro-7-methyl-2-oxoquinolin-5-yloxy)-3-[2-[(2-nitroxyethylthio)-acetylamino]-ethylamino]-propan-2-ol 1-(3-methylbenzimidazol-4-yloxy)-3-[2-[(2-nitroxyethylthio)-acetylamino]-ethylamino]-propan-2-ol 1-(2,6-dimethylindol-4-yloxy)-3-[2-[(2-nitroxyethylthio)acetylamino]-ethylamino]-propan-2-ol 1-(2-cyanophenoxy)-3-[2-[2-(2-nitroxyethylthio)-propanoylamino]-ethylamino]-propan-2-ol 1-(4-hydroxy-2,3,5-trimethylphenoxy)-3-[2-[2-(2-nitroxyethylthio)-propanoylamino]-ethylamino]-propan-2-ol 1-(2-methylindol-4-yloxy)-b 3-[2-[2-(2-nitroxyethylthio)propanoylamino]-ethylamino]-propan-2-ol 1-(1,2,3,4-tetrahydro-7-methyl-2-oxoquinolin-5-yloxy)-3-[2-[2-(2-nitroxyethylthio)-propanoylamino]-ethylamino]-propan-2-ol trans-1-(2-chloro-5-methylphenoxy)-3-[2-[(2-nitroxycyclopentylthio)-acetylamino]-ethylamino]-propan-2-ol trans-1-(6-methylindol-4-yloxy)-3-[2-[(2-nitroxycyclopentylthio)-acetylamino]-ethylamino]-propan-2-ol trans-1-(1,2-dihydro-2-oxoquinolin-5-yloxy)-3-[2-[(2-nitroxycyclopentylthio)-acetylamino]-ethylamino]-propan-2-ol trans-1-(2,6-dimethylindol-4-yloxy)-3-[2-[(2-nitroxycyclohexylthio)-acetylamino]-ethylamino]-propan-2-ol trans-1-(2-allylphenoxy)-3-[2-[(2-nitroxycyclohexylthio)acetylamino]-ethylamino]-propan-2-ol trans-1-(2-allyloxyphenoxy)-3-[2-[(2-nitroxycyclohexylthio)-acetylamino]-ethylamino]-propan-2-ol trans-1-(1-naphthyloxy)-3-[2-[(2-nitroxycyclohexylthio)acetylamino]-ethylamino]-propan-2-ol trans-1-(indol-4-yloxy)-3-[2-[(2-nitroxycyclohexylthio)acetylamino]-ethylamino]-propan-2-ol trans-1-(2-methylindol-4-yloxy)-3-[2-[(2-nitroxycyclohexylthio)-acetylamino]-ethylamino]-propan-2-ol trans-3-[2-[(2-nitroxycyclohexylthio)-acetylamino]-ethylamino]-1-(2-oxoindolin-4-yloxy)-propan-2-ol trans-1-(1,2,3,4-tetrahydro-7-methyl-2-oxoquinolin-5-yloxy)-3-[2-[(2-nitroxycyclohexylthio)-acetylamino]ethylamino]-propan-2-ol 1-(carbazol-4-yloxy)-3-[2-(4-nitroxybutanoylamino)ethylamino]-propan-2-ol 1-(2-hydroxymethylindol-4-yloxy)-3-[2-(4-nitroxybutanoylamino)-ethylamino]-propan-2-ol 1-(2-allyloxyphenoxy)-3-[1,1-dimethyl-2-(2,2-dimethyl-3-nitroxypropanoylamino)-ethylamino]-propan-2-ol 1-[4-(n-butanoylamino)-2-methylcarbonylphenoxy]-3-[1,1-dimethyl-2-(2,2-dimethyl-3-nitroxypropanoylamino)ethylamino]-propan-2-ol 1-[4-(n-butanoylamino)-2-methylcarbonylphenoxy]-3-[1,1-dimethyl-2-(4-nitroxybutanoylamino)-ethylamino]-propan-2-ol 1-[4-(n-butanoylamino)-2-methylcarbonylphenoxy]-3-[2-(2,2-dimethyl-3-nitroxypropanoylamino)-ethylamino]-propan-2-ol 3-[1,1-dimethyl-2-(2,2-dimethyl-3-nitroxypropanoylamino)ethylamino]-1-(2-oxoindolin-4-yloxy)-propan-2-ol 1-(2-cyclopentylphenoxy)-3-[1,1-dimethyl-2-[(5-O-nitroisosorbid-2-yloxy)-carbonylamino]-ethylamino]-propan-2-ol 1-(2-allylphenoxy)-3-[1,1-dimethyl-2-(3-nitroxybutanoylamino)-ethylamino]-propan-2-ol cyclamate; mp. 109°–111° C.

1-(2-allylphenoxy)-3-[1,1-dimethyl-2-(4-nitroxypentanoylamino)-ethylamino]-propan-2-ol fumarate; mp 124°–126° C.

1-(2-allylphenoxy)-3-[1,1-dimethyl-2-(5-nitroxypentanoylamino)-ethylamino]-propan-2-ol trans-1-[4-(2-methoxyethyl)-phenoxy]-3-[1,1-dimethyl-2-[(2-nitroxycyclohexyl)-acetylamino]-ethylamino]-propan-2-ol 1-[4-(2-methoxyethyl)-phenoxy]-3-[1,1-dimethyl-2-(5-nitroxypentanoylamino)-ethylamino]-propan-2-ol trans-1-(2-cyclopentylphenoxy)-3-[1,1-dimethyl-2-[(2-nitroxycyclohexyl)-acetylamino]-ethylamino]-propan-2-ol 1-(2-cyclopentylphenoxy)-3-[1,1-dimethyl-2-(5-nitroxypentanoylamino)-ethylamino]-propan-2-ol trans-3-[1,1-dimethyl-2-[(4-nitroxycyclohexyl)-carbonylamino]-ethylamino]-1-[2-(2-norbornylexo)-phenoxy]-propan-2-ol 3-[1,1-dimethyl-2-(5-nitroxypentanoylamino)-ethylamino]-1-[2-(2-norbornylexo)-phenoxy]-propan-2-ol 3-[1,1-dimethyl-2-(4-nitroxybutanoylamino)-ethylamino]-1-[2-(N-methylaminocarbonylmethoxy)-phenoxy]-propan-2-ol trans-3-[1,1-dimethyl-3-[(2-nitroxycyclohexyl)-acetylamino]-ethylamino]-1-[2-(N-methylaminocarbonylmethoxy)phenoxy]-propan-2-ol trans-3-[1,1-dimethyl-2-[(4-nitroxycyclohexyl)-carbonylamino]-ethylamino]-1-[2-(N-methylaminocarbonylmethoxy)phenoxy]-propan-2-ol 3-[1,1-dimethyl-2-(5-nitroxypentanoylamino)-ethylamino]-1-[2-(N-methylaminocarbonylmethoxy)-phenoxy]-propan-2-ol trans-1-(2-allyloxyphenoxy)-3-[1,1-dimethyl-2-[(2-nitroxycyclohexyl)-acetylamino]-ethylamino]-propan-2-ol trans-1-(2-allyloxyphenoxy)-3-[1,1-dimethyl-2-[(4-nitroxycyclohexyl)-carbonylamino]-ethylamino-propan-2-ol 1-(2-allyloxyphenoxy)-3-[1,1-dimethyl-2-(5-nitroxypentanoylamino)-ethylamino]-propan-2-ol 3-[1,1-dimethyl-2-(4-nitroxybutanoylamino)-ethylamino]-1-(2-methylthiophenoxy)-propan-2-ol trans-3-[1,1-dimethyl-2-[(4-nitroxycyclohexyl)-carbonylamino]-ethylamino]-1-(2-methylthiophenoxy)-propan-2-ol 3-[1,1-dimethyl-2-(5-nitroxypentanoylamino)-ethylamino]-1-(2-methylthiophenoxy)-propan-2-ol trans-1-(2-cyanophenoxy)-3-[1,1-dimethyl-2-[(2-nitroxycyclohexyl)-carbonylamino]-ethylamino]-propan-2-ol fumate, mp 84° C.

trans-1-(2-cyanophenoxy)-3-[1,1-dimethyl-2-[(4-nitroxycyclohexyl)-carbonylamino]-ethylamino]-propan-2-ol 1-(2-cyanophenoxy)-3-[1,1-dimethyl-2-(3-nitroxybutanoylamino)-ethylamino]-propan-2-ol cyclamate; mp 140°–142° C.

1-(2-cyanophenoxy)-3-[1,1-dimethyl-2-(5-nitroxypentanoylamino)-ethylamino]-propan-2-ol 1-(2,5-dichlorophenoxy)-3-[1,1-dimethyl-2-(4-nitroxybutanoylamino)-ethylamino]-propan-2-ol 1-(2-cyanophenoxy)-3-(1,1-dimethyl-2-[(2-nitroxyethoxy)acetylamino]-ethylamino]-propan-2-ol trans-1-(2,5-dichlorophenoxy)-3-[1,1-dimethyl-2-[(2-nitroxycyclohexyl)-acetylamino]-ethylamino]-propan-2-ol trans-1-(2,5-dichlorophenoxy)-3-[1,1-dimethyl-2-[(4-nitroxycyclohexyl)-carbonylamino]-ethylamino]-propan-2-ol 1-(2,5-dichlorophenoxy)-3-[1,1-dimethyl-2-(5-nitroxypentanoylamino)-ethylamino]-propan-2-ol 1-(2,5-dichlorophenoxy)-3-[1,1-dimethyl-2-[(2-nitroxyethoxy)-acetylamino]-ethylamino]-propan-2-ol trans-1-(2-chloro-5-methylphenoxy)-3-[1,1-dimethyl-2-[(4-nitroxycyclohexyl)-carbonylamino]-ethylamino]-propan-2-ol 1-(2-chloro-5-methylphenoxy)-3-[1,1-dimethyl-2-(3-nitroxybutanoylamino)-ethylamino]-propan-2-ol 1-(2-chloro-5-methylphenoxy)-3-[1,1-dimethyl-2-(4-nitroxypentanoylamino)-ethylamino]-propan-2-ol cyclamate; mp. 99°–101° C.

1-(2-chloro-5-methylphenoxy)-3-[1,1-dimethyl-2-(5-nitroxypentanoylamino)-ethylamino]-propan-2-ol fumarate; mp. 136°–138° C.

1-(2-chloro-5-methylphenoxy)-3-[1,1-dimethyl-3-(4-nitroxybutanoylamino)-propylamino]-propan-2-ol 1-[4-(n-butanoylamino)-2-cyanophenoxy]-3-[2-(4-nitroxybutanoylamino)-ethylamino]-propan-2-ol 1-[4-(n-butanoylamino)-2-cyanophenoxy]-3-[1,1-dimethyl-2-(4-nitroxybutanoylamino)-ethylamino]-propan-2-ol trans-1-[4-(n-butanoylamino)-2-cyanophenoxy]-3-[1,1-dimethyl-2-[(2-nitroxycyclohexyl)-acetylamino]-ethylamino]-propan-2-ol trans-1-[4-(n-butanoylamino)-2-cyanophenoxy]-3-[1,1-dimethyl-2-[(4-nitroxycyclohexyl)-carbonylamino]-ethylamino]-propan-2-ol 1-[4-(n-butanoylamino)-2-cyanophenoxy]-3-[1,1-dimethyl-2-(5-nitroxypentanoylamino)-ethylamino]-propan-2-ol trans-3-[1,1-dimethyl-2-[(2-nitroxycyclohexyl)-acetylamino]-ethylamino]-1-(4-methylcarbonyloxy-2,3,5-trimethylphenoxy)-propan-2-ol trans-1-(4-methylcarbonyloxy-2,3,5-trimethylphenoxy)-3-[2-[(4-nitroxycyclohexyl)-carbonylamino]-ethylamino]-propan-2-ol fumarate; mp. 113°–115° C.

trans-3-[1,1-dimethyl-2-[(4-nitroxycyclohexyl)-carbonylamino]-ethylamino]-1-(4-methylcarbonyloxy-2,3,5-trimethylphenoxy)-propan-2-ol 3-[1,1-dimethyl-2-(3-nitroxybutanoylamino)-ethylamino]-1-(4-methylcarbonyloxy-2,3,5-trimethylphenoxy)-propan-2-ol fumarate; mp. 95°–98° C.

3-[1,1-dimethyl-2-(5-nitroxypentanoylamino)-ethylamino]-1-(4-methylcarbonyloxy-2,3,5-trimethylphenoxy)-propan-2-ol fumarate; 125°–126° C.

trans-3-[1,1-dimethyl-2-[(2-nitroxycyclohexyl)-acetylamino]-ethylamino]-1-(4-hydroxy-2,3,5-trimethylphenoxy)-propan-2-ol fumarate; mp. 142°–144° C.

trans-3-[1,1-dimethyl-2-[(4-nitroxycyclohexyl)-carbonylamino]-ethylamino]-1-(4-hydroxy-2,3,5-trimethylphenoxy)-propan-2-ol 3-[1,1-dimethyl-2-(3-nitroxybutanoylamino)-ethylamino]-1-(4-hydroxy-2,3,5-trimethylphenoxy)-propan-2-ol 3-[1,1-dimethyl-2-(4-nitroxypentanoylamino)-ethylamino]-1-(4-hydroxy-2,3,5-trimethylphenoxy)-propan-2-ol 3-[1,1-dimethyl-2-(5-nitroxypentanoylamino)-ethylamino]-1-(4-hydroxy-2,3,5-trimethylphenoxy)-propan-2-ol fumarate; mp 133°–135° C.

trans-3-[1,1-dimethyl-2-[(2-nitroxycyclohexyl)-acetylamino]-ethylamino]-1-(1-naphthyloxy)-propan-2-ol fumarate; mp 138°–142° C.

trans-3-[1,1-dimethyl-2-[(4-nitroxycyclohexyl)-carbonylamino]-ethylamino]-1-naphthyloxy)-propan-2-ol 3-[1,1-dimethyl-2-(4-nitroxypentanoylamino)-ethylamino]-1-(1-naphthyloxy)-propan-2-ol 3-[1,1-dimethyl-2-(5-nitroxypentanoylamino)-ethylamino]-1-(1-naphthyloxy)-propan-2-ol 3-[1,1-dimethyl-3-(4-nitroxybutanoylamino)-propylamino]-1-(1-naphthyloxy)-propan-2-ol trans-3-[1,1-dimethyl-2-[(2-nitroxycyclohexyl)-acetylamino]-ethylamino]-1-(indol-4-yloxy)-propan-2-ol 1-(2-cyanoindol-4-yloxy)-3-[2-(4-nitroxybutanoylamino)ethylamino]-propan-2-ol 1-(2-cyanoindol-4-yloxy)-3-[2-(5-nitroxypentanoylamino)ethylamino]-propan-2-ol 1-(2-cyanoindol-4-yloxy)-3-[1,1-dimethyl-2-(5-nitroxypentanoylamino)-ethylamino]-propan-2-ol 1-(2,2-dimethyl-1,3-benzodioxol-4-yloxy)-3-[1,1-dimethyl-2-(4-nitroxybutanoylamino)-ethylamino]-propan-2-ol 3-[1,1-dimethyl-2-(4-nitroxybutanoylamino)-ethylamino]-1-(2-formyl-1,2,3,4-tetrahydroisoquinolin-5-yloxy)propan-2-ol 1-(1,2-dihydro-2-oxoquinolin-5-yloxy)-3-[1,1-dimethyl-2-(4-nitroxybutanoylamino)-ethylamino]-propan-2-ol 1-(1,2-dihydro-2-oxoquinolin-5-yloxy)-3-[1,1-dimethyl-2-(3-nitroxybutanoylamino)-ethylamino]-propan-2-ol 3-[2-(5-nitroxypentanoylamino)-ethylamino]-1-(1,2,3,4-tetrahydro-7-methyl-2-oxoquinolin-5-yloxy)-propan-2-ol 1-(1,2-dihydro-7-methyl-2-oxoquinolin-5-yloxy)-3-[1,1-dimethyl-2-(4-nitroxybutanoylamino)-ethylamino]-propan-2-ol 1-(1,2-dihydro-7-methyl-2-oxoquinolin-5-yloxy)-3-[1,1-dimethyl-2-(5-nitroxypentanoylamino)-ethylamino]-propan-2-ol 1-(8-acetylamino-2-oxo-1,2,3,4-tetrahydroquinolin-5-yloxy)-3-[2-(4-nitroxybutanoylamino)-ethylamino]-propan-2-ol 1-(8-acetylamino-2-oxo-1,2,3,4-tetrahydroquinolin-5-yloxy)-3-[2-(5-nitroxypentanoylamino)-ethylamino]-propan-2-ol 1-(8-acetylamino-2-oxo-1,2,3,4-tetrahydroquinolin-5-yloxy)-3-[1,1-dimethyl-2-(4-nitroxybutanoylamino)-ethylamino]-propan-2-ol ·

1-(3-cyano-1,2-dihydro-2-oxoquinolin-5-yloxy)-3-[2-(4-nitroxybutanoylamino)-ethylamino]-propan-2-ol 1-(3-cyano-1,2-dihydro-2-oxoquinolin-5-yloxy)-3-[1,1-dimethyl-2-(4-nitroxybutanoylamino)-ethylamino]-propan-2-ol 1-(3-cyano-1,2-dihydro-2-oxoquinolin-5-yloxy)-3-[1,1-dimethyl-2-(5-nitroxypentanoylamino)-ethylamino]-propan-2-ol 1-(3-cyano-1,2-dihydro-7-methyl-2-oxoquinolin-5-yloxy)-3-[2-(4-nitroxybutanoylamino)-ethylamino]-propan-2-ol 1-(3-cyano-1,2-dihydro-7-methyl-2-oxoquinolin-5-yloxy)-3-[2-(5-nitroxypentanoylamino)-ethylamino]-propan-2-ol 1-(3-cyano-1,2-dihydro-7-methyl-2-oxoquinolin-5-yloxy)-3-[1,1-dimethyl-2-(4-nitroxybutanoylamino)-ethylamino]-propan-2-ol 1-(3-cyano-1,2-dihydro-7-methyl-2-oxoquinolin-5-yloxy)-3-[1,1-dimethyl-2-(5-nitroxypentanoylamino)-ethylamino]-propan-2-ol 1-(3,4-dihydro-2H-3-oxo-1,4-benzthiazin-8-yloxy)-3-[2-(4-nitroxybutanoylamino)-ethylamino]-propan-2-ol 1-(3,4-dihydro-2H-3-oxo-1,4-benzthiazin-8-yloxy)-3-[2-(5-nitroxypentanoylamino)-ethylamino]-propan-2-ol 1-(3,4-dihydro-2H-3-oxo-1,4-benzthiazin-8-yloxy)-3-[1,1-dimethyl-2-(4-nitroxybutanoylamino)-ethylamino]-propan-2-ol 1-(3,4-dihydro-2H-3-oxo-1,4-benzthiazin-8-yloxy)-3-[1,1-dimethyl-2-(5-nitroxypentanoylamino)-ethylamino]-propan-2-ol 1-(3-cyano-2H-benzypyran-8-yloxy)-3-[2-(4-nitroxybutanoylamino)-ethylamino]-propan-2-ol trans-1-(3-cyano-2H-benzpyran-8-yloxy)-3-[2-[(4-nitroxycyclohexyl)-carbonylamino]-ethylamino]-propan-2-ol 1-(3-cyano-2H-benzpyran-8-yloxy)-3-[2-(3-nitroxybutanoylamino)-ethylamino]-propan-2-ol 1-(3-cyano-2H-benzpyran-8-yloxy)-3-[1,1-dimethyl-2-(4-nitroxybutanoylamino)-ethylamino]-propan-2-ol 1-(3-cyano-2H-benzpyran-8-yloxy)-3-[1,1-dimethyl-2-(3-nitroxybutanoylamino)-ethylamino]-propan-2-ol 1-(3-cyano-2H-benzpyran-8-yloxy)-3-[1,1-dimethyl-2-(5-nitroxypentanoylamino)-ethylamino]-propan-2-ol trans-1-(3-methylbenzimidazol-4-yloxy)-3-[2-[(4-nitroxycyclohexyl)-carbonylamino]-ethylamino]-propan-2-ol trans-1-(3-methylbenzimidazol-4-yloxy)-3-[1,1-dimethyl-2-[(2-nitroxycyclohexyl)-acetylamino]-ethylamino]-propan-2-ol 1-(1,2-dihydro-2-oxo-1,3-benzdiazin-5-yloxy)-3-[2-(4-nitroxybutanoylamino)-ethylamino]-propan-2-ol 1-(1,2-dihydro-2-oxo-1,3-benzdiazin-5-yloxy)-3-[1,1-dimethyl-2-(4-nitroxybutanoylamino)-ethylamino]-propan-2-ol trans-1-(1,2-dihydro-2-oxo-1,3-benzdiazin-5-yloxy)-3-[1,1-dimethyl-2-[(2-nitroxycyclohexyl)-acetylamino]ethylamino]-propan-2-ol 1-(3,4-dihydro-2,2-dioxo-1,2-benzoxathiin-5-yloxy)-3-[2-(4-nitroxybutanoylamino)-ethylamino]-propan-2-ol 1-(3,4-dihydro-2,2-dioxo-1,2-benzoxathiin-5-yloxy)-3-[1,1-dimethyl-2-(4-nitroxybutanoylamino)-ethylamino]-propan-2-ol 1-(3,4-dihydro-2,2-dioxo-1,2-benzoxathiin-8-yloxy)-3-[1,1-dimethyl-2-(4-nitroxybutanoylamino)-ethylamino]-propan-2-ol 1-(3,4-dihydro-2,2-dioxo-1H-1-methyl-2,1-benzthiazin-5-yloxy)-3-[2-(4-nitroxybutanoylamino)-ethylamino]-propan-2-ol 1-(3,4-dihydro-2,2-dioxo-1H-1-methyl-2,1-benzthiazin-5-yloxy)-3-[1,1-dimethyl-2-(4-nitroxybutanoylamino)-ethylamino]-propan-2-ol trans-1-(carbazol-4-yloxy)-3-[2-[(4-nitroxycyclohexyl)-carbonylamino]-ethylamino]-propan-2-ol 3-[1,1-dimethyl-2-(4-nitroxybutanoylamino)-ethylamino]-1-(1-oxoindan-7-yloxy)-propan-2-ol 3-[1,1-dimethyl-2-(3-nitroxybutanoylamino)-ethylamino]-1-(1-oxoindan-7-yloxy)-propan-2-ol 3-[1,1-dimethyl-2-(5-nitroxypentanoylamino)-ethylamino]-1-(1-oxoindan-7-yloxy)-propan-2-ol 3-[1,1-dimethyl-2-(4-nitroxybutanoylamino)-ethylamino]-1-(2-methoxyphenoxy)-propan-2-ol cyclamate; mp. 105°–107° C.

trans-3-[1,1-dimethyl-2-[(2-nitroxycyclohexyl)-acetylamino]-ethylamino]-1-(2-methoxyphenoxy)-propan-2-ol 3-[1,1-dimethyl-2-(3-nitroxybutanoylamino)-ethylamino]-1-(2-methoxyphenoxy)-propan-2-ol 3-[1,1-dimethyl-2-(5-nitroxypentanoylamino)-ethylamino]-1-(2-methoxyphenoxy)-propan-2-ol 3-[1,1-dimethyl-2-(4-nitroxybutanoylamino)-ethylamino]-1-(2-propargyloxyphenoxy)-propan-2-ol 3-[1,1-dimethyl-2-(4-nitroxybutanoylamino)-ethylamino]-1-(2-methylphenoxy)-propan-2-ol cyclamate; mp. 126°–128° C.

3-[1,1-dimethyl-2-(4-nitroxybutanoylamino)-ethylamino]-1-(3-methylphenoxy)-propan-2-ol cyclamate; mp. 114°–116° C.

3-[1,1-dimethyl-2-(4-nitroxybutanoylamino)-ethylamino]-1-(1,2,3,4-tetrahydro-1-oxo-5-naphthyloxy)-propan-2-ol 3-[1,1-dimethyl-2-(4-nitroxybutanoylamino)-ethylamino]-1-(3,4-dihydro-2H-benzthiin-8-yloxy)-propan-2-ol 1-(1,2-benzthiazol-4-yloxy)-3-[1,1-dimethyl-2-(4-nitroxybutanoylamino)-ethylamino]-propan-2-ol 1-(1,3-benzthiazol-7-yloxy)-3-[1,1-dimethyl-2-(4-nitroxybutanoylamino)-ethylamino]-propan-2-ol trans-1-(2-cyanophenoxy)-3-[1,1-dimethyl-2-[(2-nitroxycyclohexyloxy)-carbonylamino]-ethylamino]-propan-2-ol 1-(2-cyanophenoxy)-3-[1,1-dimethyl-2-[(4-nitroxymethylpiperidin-1-yl)-carbonylamino]-ethylamino]-propan-2-ol 3-[1,1-dimethyl-2-[[4-(1-nitroxyethyl)-piperidin-1-yl]-carbonylamino]-ethylamino]-1-(4-methylcarbonyloxy-2,3,5-trimethylphenoxy)-propan-2-ol 3-[1,1-dimethyl-2-[(4-nitroxymethylpiperidin-1-yl)-carbonylamino]-ethylamino]-1-(2-methoxyphenoxy)-propan-2-ol trans-1-(2,3-dichlorophenoxy)-3-[1,1-dimethyl-2-(2-nitroxycyclohexylamino)-ethylamino]-propan-2-ol 1-(2H-3,4-dihydrobenzopyran-8-yloxy)-3-[2-(4-nitroxybutanoylamino)-ethylamino]-propan-2-ol 1-(2H-3,4-dihydrobenzopyran-8-yloxy)-3-[1,1-dimethyl-2-(4-nitroxybutanoylamino)-ethylamino]-propan-2-ol trans-1-(2H-3,4-dihydrobenzopyran-8-yloxy)-3-[1,1-dimethyl-2-[(4-nitroxycyclohexyl)-carbonylamino]ethylamino]-propan-2-ol 1-(3-methyl-1,2-benzisoxazol-4-yloxy)-3-[2-(4-nitroxybutanoylamino)-ethylamino]-propan-2-ol 3-[1,1-dimethyl-2-(4-nitroxybutanoylamino)-ethylamino]-1-(3-methyl-1,2-benzisoxazol-4-yloxy)-propan-2-ol.

The following Examples are given for the purpose of illustrating the present invention:

EXAMPLE 1

1-(3-Cyanoindol-4-yloxy)-3-[2-(3-nitroxybutanoylamino)-ethylamino]-propan-2-ol fumarate 4.2 g. 1-(3-cyanoindol-4-yloxy)-2,3-epoxypropane (see European patent specification No. 0,045,910) are suspended in 100 ml. n-butanol, mixed with 11.5 g. 2-(3-nitroxybutanoylamino)-ethylamine and stirred for 2 days at ambient temperature. After removal of the solvent, the residue is chromatographed on silica gel with methylene chloride/methanol (95:5 v/v) and methylene chloride/methanolic ammonia solution (95:5 v/v). From the appropriate fractions, after removal of the solvent, there are obtained 4.6 g. of base. By dissolving in methanol and adding the calculated amount of fumaric acid, there are obtained, after suction filtration, 3.9 g. (40% of theory) of the desired fumarate; m.p. 155°–156° C.

EXAMPLE 2

In a manner analogous to that described in Example 1, from 1-aryloxy-2,3-epoxypropanes or 1-hetaryloxy-2,3-epoxypropanes (see, for example, European patent specification No. 0,045,910, Federal Republic of Germany patent specifications Nos. 33 10 891 and 25 08 251, European patent specification No. 0,014,951, Federal Republic of Germany patent specifications Nos. 25 03 222; 16 20 342; 26 26 890 and 23 62 278; J. Med. Chem., 17, 529/1974; J. Med. Chem., 26, 1570/1983; WHO Chronicle, 26, 1125/1972; Federal Republic of Germany patent specification No. 27 35 570; Chem. Pharm. Bull., 20, 905/1972; European patent specification No. 0,095,454) and nitroxyalkanoylaminoalkylamines, there are obtained the following compounds:

| designation | yield % | melting point °C. (solvent) |
|---|---|---|
| 1. 3-[2-(3-nitroxybutanoyl-amino)-ethylamino]-1-(2-oxo-indolin-4-yloxy)-propan-2-ol hemifumarate from 2,3-epoxy-1-(2-oxo-indolin-4-yloxy)-propane and 2-(3-nitroxybutanoylamino)-ethylamine | 27 | 165–167 (ethanol) |
| 2. 1-(2-allylphenoxy)-3-[2-(4-nitroxybutanoylamino)-ethyl-amino]-propan-2-ol from 1-(2-allylphenoxy)-2,3-epoxypropane and 2-(4-nitroxy-butanoylamino)-ethylamine | 18 | 117–119 (ethyl acetate) |
| 3. 1-[4-(2-methoxyethyl)-phenoxy]-3-[2-(4-nitroxybutanoylamino)-ethylamino]-propan-2-ol tropate from 2,3-epoxy-1-[4-(2-methoxy-ethyl)-phenoxy]-propane and 2-(4-nitroxybutanoylamino)-ethyl-amine | 10 | 88–90 (ethyl acetate/ diethyl ether) |
| 4. 1-(2-cyclopentylphenoxy)-3-[2-(4-nitroxybutanoylamino)-ethylamino]-propan-2-ol citrate from 1-(2-cyclopentylphenoxy)-2,3-epoxypropane and 2-(4-nitroxybutanoylamino)-ethylamine | 14 | 123–125 (acetone/ diethyl ether 1:1 v/v) |
| 5. 1-(2-allyloxyphenoxy)-3-[2-(4-nitroxybutanoylamino)-ethyl-amino]-propan-2-ol from 1-(2-allyloxyphenoxy)-2,3-epoxypropane and 2-(4-nitroxy-butanoylamino)-ethylamine | 11 | oil |
| 6. 1-(2-cyanophenoxy)-3-[2-(4-nitroxybutanoylamino)-ethyl-amino]-propan-2-ol from 1-(2-cyanophenoxy)-2,3-epoxypropane and 2-(4-nitroxy-butanoylamino)-ethylamine | 20 | 108–110 (ethyl acetate) |
| 7. 1-(2-chloro-5-methylphenoxy)-3-[2-(4-nitroxybutanoylamino)-ethylamino]-propan-2-ol from 1-(2-chloro-5-methyl-phenoxy)-2,3-epoxypropane and 2-(4-nitroxybutanoylamino)-ethylamine | 30 | 98–100 (ethyl acetate) |
| 8. 1-[4-(n-butanoylamino)-2-methyl-carbonylphenoxy]-3-[2-(4-nitroxybutanoylamino)ethyl-amino]-propan-2-ol from 1-[4-(n-butanoylamino)-2-methylcarbonylphenoxy]-2,3-epoxypropane and 2-(4-nitroxy-butanoylamino)-ethylamine | 10 | oil |
| 9. 1-(4-methylcarbonyloxy-2,3,5-trimethylphenoxy)-3-[2-(4-nitroxybutanoylamino)-ethyl-amino]-propan-2-ol from 2,3-epoxy-1-(4-methyl-carbonyloxy-2,3,5-trimethyl-phenoxy)-propane and 2-(4-nitroxybutanoylamino)-ethyl-amine | 47 | 105–107 (n-butanol) |
| 10. 1-(1-naphthyloxy)-3-[2-(4-nitroxybutanoylamino)-ethyl-amino]-propan-2-ol cyclamate from 2,3-epoxy-1-(1-naphthyl-oxy)-propane and 2-(4-nitroxy-butanoylamino)-ethylamine | 15 | 114–116 (ethyl acetate) |
| 11. 1-indol-4-yloxy)-3-[2-(4-nitroxybutanoylamino)-ethyl-amino]-propan-2-ol hemi-fumarate from 2,3-epoxy-1-(indol-4-yloxy)-propane and 2-(4-nitroxybutanoylamino)-ethyl-amine | 27 | 130–131 (methanol) |
| 12. 1-(2-methylindol-4-yloxy)-3-[2-(4-nitroxybutanoylamino)-ethyl-amino]-propan-2-ol cyclamate from 2,3-epoxy-1-(2-methyl-indol-4-yloxy)-propane and 2-(4-nitroxybutanoylamino)-ethyl-amine | 30 | 120–121 (ethyl acetate) |
| 13. 1-(6-methylindol-4-yloxy)-3-[2-(4-nitroxybutanoylamino)-ethyl-amino]-propan-2-ol fumarate from 2,3-epoxy-1-(6-methyl-indol-4-yloxy)-propane and 2-(4-nitroxybutanoylamino)-ethylamine | 25 | 132–133 (methanol) |
| 14. 1-(2,6-dimethylindol-4-yloxy)-3-[2-(4-nitroxybutanoylamino)-ethylamino]-propan-2-ol-cyclamate from 1-(2,6-dimethylindol-4-yloxy)-2,3-epoxypropane and 2-(4-nitroxybutanoylamino)-ethylamine | 53 | 135 (ethyl acetate) |
| 15. 1-(3-cyanoindol-4-yloxy)-3-[2-(4-nitroxybutanoylamino)-ethylamino]-propan-2-ol hemi-fumarate from 1-(3-cyanoindol-4-yloxy)-2,3-epoxypropane and 2-(4-nitroxybutanoylamino)-ethylamine | 50 | 108–110 (ethyl acetate) |
| 16. 1-(3-cyano-6-methylindol-4-yloxy)-3-[2-(4-nitroxy-butanoylamino)-ethylamino]-propan-2-ol cyclemate from 1-(3-cyano-6-methyl-indol-4-yloxy)-2,3-epoxy-propane and 2-(4-nitroxy-butanoylamino)-ethylamine | 33 | 138–140 (ethanol) |
| 17. 3-[2-(4-nitroxybutanoylamino)-ethylamino]-1-(2-oxoindolin-4-yloxy)-propan-2-ol fumarate from 2,3-epoxy-1-(2-oxoindolin-4-yloxy)-propane and 2-(4-nitroxybutanoylamino)-ethyl-amine | 35 | 138–139 (methanol) |
| 18. 1-(1,2,3,4-tetrahydro-2-oxo-quinolin-5-yloxy)-3-[2-(4-nitroxybutanoylamino)-ethyl-amino]-propan-2-ol fumarate from 1-(1,2,3,4-tetrahydro-2-oxoquinolin-5-yloxy)-2,3-epoxypropane and 2-(4-nitroxy-butanoylamino)-ethylamine | 53 | 135 (ethanol) |
| 19. 1-(1,2-dihydro-2-oxoquinolin-5-yloxy)-3-[2-(4-nitroxy-butanoylamino)-ethylamino]-propan-2-ol cyclamate from 1-(1,2-dihydro-2-oxo-quinolin-5-yloxy)-2,3-epoxy-propane and 2-(4-nitroxy-butanoylamino)-ethylamine | 10 | 128 (methanol) |
| 20. 1-(1,2,3,4-tetrahydro-7-methyl- | 44 | 138–140 |

-continued

| | designation | yield % | melting point °C. (solvent) |
|---|---|---|---|
| | 2-oxoquinolin-5-yloxy)-3-[2-(4-nitroxybutanoylamino)-ethylamino]-propan-2-ol fumarate from 1-(1,2,3,4-tetrahydro-7-methyl-2-oxoquinolin-5-yloxy)-2,3-epoxypropane and 2-(4-nitroxybutanoylamino)-ethylamine | | (ethanol) |
| 21. | 1-(1,2-dihydro-7-methyl-2-oxoquinolin-5-yloxy)-3-[2-(4-nitroxybutanoylamino)-ethylamino]-propan-2-ol fumarate from 1-(1,2-dihydro-7-methyl-2-oxoquinolin-5-yloxy)-2,3-epoxypropane and 2-(4-nitroxybutanoylamino)-ethylamine | 20 | 145 (ethanol) |
| 22. | 1-(3-methylbenzimidazol-4-yloxy)-3-[2-nitroxybutanoylamino)-ethylamino]-propan-2-ol cyclamate from 2,3-epoxy-1-(3-methylbenzimidazol-4-yloxy)-propane and 2-(4-nitroxybutanoylamino)-ethylamine | 3 | 90–93 (toluene/diethyl ether 1:1) |
| 23. | 1-(2-formyl-1,2,3,4-tetrahydroisoquinolin-5-yloxy)-3-[2-(4-nitroxybutanoylamino)-ethylamino]-propan-2-ol from 2,3-epoxy-1-(2-formyl-1,2,3,4-tetrahydroisoquinolin-5-yloxy)-propane and 2-(4-nitroxybutanoylamino)-ethylamine | 47 | 122–123 (acetone) |
| 24. | 1-(2-methylindol-4-yloxy)-3-[3-(4-nitroxybutanoylamino)-propylamino]-propan-2-ol cyclamate from 2,3-epoxy-1-(2-methylindol-4-yloxy)-propane and 3-(4-nitroxybutanoylamino)-propylamine | 5 | 119–121 (ethanol) |
| 25. | 3-[3-(4-nitroxybutanoylamino)-propylamino]-1-(2-oxoindolin-4-yloxy)-propan-2-ol cyclamate from 2,3-epoxy-1-(2-oxoindolin-4-yloxy)-propane and 3-(4-nitroxybutanoylamino)-propylamine | 5 | 122–125 (ethanol) |
| 26. | 1-(3-cyanoindol-4-yloxy)-3-[2,2-dimethyl-3-(4-nitroxybutanoylamino)-propylamino]-propan-2-ol fumarate from 1-(3-cyanoindol-4-yloxy)-2,3-epoxypropane and 2,2-dimethyl-3-(4-nitroxybutanoylamino)-propylamine | 15 | 119–120 (ethanol) |
| 27. | 3-[2,2-dimethyl-3-(4-nitroxybutanoylamino)-propylamino]-1-(2-oxoindolin-4-yloxy)-propan-2-ol fumarate from 2,3-epoxy-1-(2-oxoindolin-4-yloxy)-propane and 2,2-dimethyl-3-(4-nitroxybutanoylamino)-propylamine | 30 | 117–118 (ethanol) |
| 28. | 1-(3-cyanoindol-4-yloxy)-3-[2-(4-nitroxypentanoylamino)-ethylamino]-propan-2-ol cyclamate from 1-(3-cyanoindol-4-yloxy)-2,3-epoxypropane and 2-(4-nitroxypentanoylamino)-ethylamine | 20 | 137–138 (ethanol) |
| 29. | 3-[2-(4-nitroxypentanoylamino)-ethylamino]-1-(2-oxoindolin-4-yloxy)-propan-2-ol cyclamate from 2,3-epoxy-1-(2-oxoindolin-4-yloxy)-propane and 2-(4-nitroxypentanoylamino)-ethylamine | 20 | 137–138 (ethanol) |
| 30. | 1-(3-cyanoindol-4-yloxy)-3-[2-(5-nitroxypentanoylamino)-ethylamino]-propan-2-ol hemifumarate from 1-(3-cyanoindol-4-yloxy)-2,3-epoxypropane and 2-(5-nitroxypentanoylamino)-ethylamine | 52 | 156–160 (propan-2-ol) |
| 31. | 3-[2-(5-nitroxypentanoylamino)-ethylamino]-1-(2-oxoindolin-4-yloxy)-propan-2-ol hemifumarate from 2,3-epoxy-1-(2-oxoindolin-4-yloxy)-propane and 2-(5-nitroxypentanoylamino)-ethylamine | 30 | 162–164 (ethanol) |
| 32. | 1-(3-cyanoindol-4-yloxy)-3-[2-(3,3-dimethyl-2,4-dinitroxybutanoylamino)-ethylamino]-propan-2-ol fumarate from 1-(3-cyanoindol-4-yloxy)-2,3-epoxypropane and 2-(3,3-dimethyl-2,4-dinitroxybutanoylamino)-ethylamine | 20 | 50–55 (propan-2-ol) |
| 33. | 3-[2-(3,3-dimethyl-2,4-dinitroxybutanoylamino)-ethylamino]-1-(2-oxoindolin-4-yloxy)-propan-2-ol hemifumarate from 2,3-epoxy-1-(2-oxoindolin-4-yloxy)-propane and 2-(3,3-dimethyl-2,4-dinitroxybutanoylamino)-ethylamine | 20 | 127–129 (propan-2-ol) |
| 34. | trans-3-[2-[(2-nitroxycyclohexyl)-acetylamino]-ethylamino]-1-(2-oxoindolin-4-yloxy)-propan-2-ol hemifumarate from 2,3-epoxy-1-(2-oxoindolin-4-yloxy)-propane and trans-2-[(2-nitroxycyclohexyl)-acetylamino]-ethylamine | 35 | 151–153 (methanol) |
| 35. | 3-[2-(4-nitroxybutanoylamino)-ethylamino]-1-(1-oxoindan-7-yloxy)-propan-2-ol cyclamate from 2,3-epoxy-1-(1-oxoindan-7-yloxy)-propane and 2-(4-nitroxybutanoylamino)-ethylamine | 6 | 104–105 (ethanol) |
| 36. | 1-(5-methyl-1-oxoindan-7-yloxy)-3-[2-(4-nitroxybutanoylamino)-ethylamino]-propan-2-ol cyclamate from 2,3-epoxy-1-(5-methyl-1-oxoindan-7-yloxy)-propane and 2-(4-nitroxybutanoylamino)-ethylamine | 10 | 116–118 (ethyl acetate) |
| 37. | 1-(indol-4-yloxy)-3-[2-(2-methyl-4-nitroxybutanoylamino)-ethylamino]-propan-2-ol cyclamate from 2,3-epoxy-1-(indol-4-yloxy)-propane and 2-(2-methyl-4-nitroxybutanoylamino)-ethylamine | 10 | 107 (propan-2-ol) |
| 38. | 1-(3,6-dimethylindol-4-yloxy)-3-[2-(4-nitroxybutanoylamino)-ethylamino]-propan-2-ol cyclamate from 1-(3,6-dimethylindol-4-yloxy)-2,3-epoxypropane and 2-(4-nitroxybutanoylamino)-ethylamine | 50 | 135 (ethyl acetate) |
| 39. | 1-(indol-4-yloxy)-3-[2,2-dimethyl-3-(4-nitroxybutanoylamino)-propylamino]-propan-1-ol hemifumarate from 2,3-epoxy-1-(indol-4-yloxy)-propane and 2,2-dimethyl-3-(4-nitroxybutanoylamino)-propylamine | 32 | 136–138 (ethanol) |
| 40. | 1-(6-methylindol-4-yloxy)-3-[2-(3-nitroxybutanoylamino)-ethylamino]-propan-2-ol cyclamate from 2,3-epoxy-1-(6-methylindol-4-yloxy)-propane and 2-(3-nitroxybutanoylamino)-ethylamine | 38 | 166 (ethanol) |

-continued

| | designation | yield % | melting point °C. (solvent) |
|---|---|---|---|
| 41. | 1-(2-methylindol-4-yloxy)-3-[2-(5-nitroxypentanoylamino)-ethylamino]-propan-2-ol cyclamate from 2,3-epoxy-1-(2-methylindol-4-yloxy)-propane and 2-(5-nitroxypentanoylamino)-ethylamine | 48 | 135–137 (ethanol) |
| 42. | 3-[1,1-dimethyl-2-(4-nitroxybutanoylamino)-ethylamino]-1-(indol-4-yloxy)-propan-1-ol cyclamate from 2,3-epoxy-1-(indol-4-yloxy)-propane and 1,1-dimethyl-2-(4-nitroxybutanoylamino)-ethylamine | 50 | 108–110 (ethanol) |
| 43. | 1-(2-chloro-5-methylphenoxy)-3-[2-(5-nitroxypentanoylamino)-ethylamino]-propan-2-ol cyclamate from 1-(2-chloro-5-methylphenoxy)-2,3-epoxypropane and 2-(5-nitroxypentanoylamino)-ethylamine | 14 | 111 (acetone) |
| 44. | trans-1-[4-(2-methoxyethyl)-phenoxy]-3-[2-[(2-nitroxycyclohexyl)-acetylamino]-ethylamino]-propan-2-ol from 2,3-epoxy-1-[4-(2-methoxyethyl)-phenoxy]-propane and trans-2-[(2-nitroxycyclohexyl)-acetylamino]-ethylamine | 36 | 107–109 (ethyl acetate) |
| 45. | trans-1-(2-allylphenoxy)-3-[2-[(2-nitroxycyclohexyl)-acetylamino]-ethylamino]-propan-2-ol from 1-(2-allylphenoxy)-2,3-epoxypropane and trans-2-[(2-nitroxycyclohexyl)-acetylamino]-ethylamine | 36 | 103–105 (ethyl acetate) |
| 46. | 1-(2-chloro-5-methylphenoxy)-3-[1,1-dimethyl-2-(4-nitroxybutanoylamino)-ethylamino]-propan-2-ol cyclamate from 1-(2-chloro-5-methylphenoxy)-2,3-epoxypropane and 1,1-dimethyl-2-(4-nitroxybutanoylamino)-ethylamine | 39 | 108–110 (ethyl acetate) |
| 47. | 1-(2,5-dichlorophenoxy)-3-[2-(4-nitroxybutanoylamino)-ethylamino]-propan-2-ol from 1-(2,5-dichlorophenoxy)-2,3-epoxypropane and 2-(4-nitroxybutanoylamino)-ethylamine | 60 | 125–127 (acetone) |
| 48. | 1-(2-cyanophenoxy)-3-[1,1-dimethyl-2-(4-nitroxybutanoylamino)-ethylamino]-propan-2-ol fumarate from 1-(2-cyanophenoxy)-2,3-epoxypropane and 1,1-dimethyl-2-(4-nitroxybutanoylamino)-ethylamine | 55 | 140–145 (ethyl acetate) |
| 49. | 3-[2-(3,3-dimethyl-5-nitroxypentanoylamino)-ethylamino]-1-(4-methylcarbonyloxy-2,3,5-trimethylphenoxy)-propan-2-ol fumarate from 2,3-epoxy-1-(4-methylcarbonyloxy-2,3,5-trimethylphenoxy)-propane and 2-(3,3-dimethyl-5-nitroxypentanoylamino)-ethylamine | 20 | 120–122 (ethyl acetate) |
| 50. | trans-1-(2-allylphenoxy)-3-[1,1-dimethyl-2-[(2-nitroxycyclohexyl)-acetylamino]-ethylamino]-propan-2-ol fumarate from 1-(2-allylphenoxy)-2,3-epoxypropane and trans-1,1-dimethyl-2-[(2-nitroxycyclohexyl)-acetylamino]-ethylamine | 12 | 130–132 (ethyl acetate) |
| 51. | 1-(2-allylphenoxy)-3-[1,1-dimethyl-2-(3-nitroxybutanoylamino)-ethylamino]-propan-2-ol fumarate from 1-(2-allylphenoxy)-2,3-epoxypropane and 1,1-dimethyl-2-(3-nitroxybutanoylamino)-ethylamine | 41 | 121–123 (ethyl acetate) |
| 52. | 1-(2-chloro-5-methylphenoxy)-3-[1,1-dimethyl-2-(3-nitroxybutanoylamino)-ethylamino]-propan-2-ol fumarate from 1-(2-chloro-5-methylphenoxy)-2,3-epoxypropane and 1,1-dimethyl-2-(3-nitroxybutanoylamino)-ethylamine | 66 | 144–147 (ethyl acetate) |
| 53. | 3-[1,1-dimethyl-2-(3-nitroxy butanoylamino)-ethylamino]-1-(1-naphthyloxy)-propan-2-ol fumarate from 2,3-epoxy-1-(1-naphthyloxy)-propane and 1,1-dimethyl-3-(3-nitroxybutanoylamino)-ethylamine | 32 | 110–112 (ethyl acetate) |
| 54. | 3-[1,1-dimethyl-2-(4-nitroxybutanoylamino)-ethylamino]-1-(1,2,3,4-tetrahydro-2-oxoquinolin-5-yloxy)-propan-2-ol fumarate from 2,3-epoxy-1-(1,2,3,4-tetrahydro-2-oxoquinolin-5-yloxy)-propane and 1,1-dimethyl-2-(4-nitroxybutanoylamino)-ethylamine | 10 | 132–134 (ethanol) |
| 55. | 3-[1,1-dimethyl-2-(4-nitroxybutanoylamino)-ethylamino]-1-(2-oxoindolin-4-yloxy)-propan-2-ol fumarate from 2,3-epoxy-1-(2-oxoindolin-4-yloxy)-propane and 1,1-dimethyl-2-(4-nitroxybutanoylamino)-ethylamine | 25 | 120–122 (ethanol) |
| 56. | 3-[2-(4-nitroxybutanoylamino)-ethylamino]-1-[2-(2-norbornylexo)-phenoxy]-propan-2-ol cyclamate from 2,3-epoxy-1-[2-(2-norbornylexo)-phenoxy]-propane and 2-(4-nitroxybutanoylamino)-ethylamine | 46 | 117–118 (ethyl acetate/ diethyl ether 1:2 v/v) |
| 57. | 3-[1,1-dimethyl-2-(4-nitroxybutanoylamino)-ethylamino]-1-[2-(2-norbornylexo)-phenoxy]-propan-2-ol fumarate from 2,3-epoxy-1-[2-(2-norbornylexo)-phenoxy]-propane and 1,1-dimethyl-2-(4-nitroxybutanoylamino)-ethylamine | 24 | 138–140 (ethyl acetate) |
| 58. | trans-3-[1,1-dimethyl-2-[(2-nitroxycyclohexyl)-acetylamino]-ethylamino]-1-(2H-5-methyl-2-oxobenzo[e]pyran-8-yloxy)-propan-2-ol fumarate from 2,3-epoxy-1-(2H-5-methyl-2-oxobenzo[e]pyran-8-yloxy)-propane and 1,1-dimethyl-2-[(2-nitroxycyclohexyl)-acetylamino]-ethylamine | 58 | 170(decomp.) (ethyl acetate) |
| 59. | 3-[1,1-dimethyl-2-(4-nitroxybutanoylamino)-ethylamino]-1-(2H-5-methyl-2-oxobenzo[e]pyran-8-yloxy)-propan-2-ol cyclamate from 2,3-epoxy-1-(2H-5-methyl-2-oxobenzo[e]pyran-8-yloxy)-propane and 1,1-dimethyl-2-(4-nitroxybutanoylamino)-ethylamine | 50 | 120–122 (ethyl acetate) |
| 60. | 1-(2H-5-methyl-2-oxobenzo[e]pyran-8-yloxy)-3-[2-(4-nitroxy | 39 | 66–68 (ethyl |

-continued

| | designation | yield % | melting point °C. (solvent) |
|---|---|---|---|
| | butanoylamino)-ethylamino]-propan-2-ol from 2,3-epoxy-1-(2H-5-methyl-2-oxobenzo[e]pyran-8-yloxy)-propane and 2-(4-nitroxy-butanoylamino)-ethylamine | | acetate) |
| 61. | trans-1-(2-chloro-5-methyl-phenoxy)-3-[1,1-dimethyl-2-[(2-nitroxy-cyclohexyl)-acetylamino]-ethylamino]-propan-2-ol fumarate from 1-(2-chloro-5-methyl-phenoxy)-2,3-epoxypropane and 1,1-dimethyl-2-[(2-nitroxy-cyclohexyl)-acetylamino]-ethylamine | 28 | 134–136 (acetone/ diethyl ether 5:2 v/v) |
| 62. | 1-(2,2-dimethyl-1,3-benzdioxol-4-yloxy)-3-[2-(4-nitroxy-butanoylamino)-ethylamino]-propan-2-ol fumarate from 1-(2,2-dimethyl-1,3-benz-dioxol-4-yloxy)-2,3-epoxy-propane and 2-(2-nitroxy-butanoylamino)-ethylamine | 32 | 123–125 (ethyl acetate) |
| 63. | 1-(2-allyloxyphenoxy)-3-[1,1-dimethyl-2-(4-nitroxy-butanoylamino)-ethylamino]-propan-2-ol fumarate from 1-(2-allyloxyphenoxy)-2,3-epoxypropane and 1,1-dimethyl-2-(4-nitroxybutanoylamino)-ethylamine | 57 | 115–117 (ethyl acetate) |
| 64. | 3-[1,1-dimethyl-2-(4-nitroxy-butanoylamino)-ethylamino]-1-[4-(2-methoxyethyl)-phenoxy]-propan-2-ol fumarate from 2,3-epoxy-1-[4-(2-methoxyethyl)-phenoxy]-propane and 1,1-dimethyl-2-(4-nitroxy-butanoylamino)-ethylamine | 40 | 128–130 (ethyl acetate) |
| 65. | 1-(2,5-dichlorophenoxy)-3-[1,1-dimethyl-2-(4-nitroxy-butanoylamino)-ethylamino]-propan-2-ol fumarate from 1-(2,5-dicholorophenoxy)-2,3-epoxypropane and 1,1-dimethyl-2-(4-nitroxy-butanoylamino)-ethylamine | 66 | 138–140 (ethyl acetate) |
| 66. | 1-(2-cyanophenoxy)-3-[2-(3-nitroxybutanoylamino)-ethyl-amino]-propan-2-ol fumarate from 1-(2-cyanophenoxy)-2,3-epoxypropane and 2-(3-nitroxybutanoylamino)-ethyl-amine | 23 | 140–143 (acetone) |
| 67. | 1-(indol-4-yloxy)-3-[2-(3-nitroxybutanoylamino)-ethyl-amino]-propan-2-ol cyclamate from 2,3-epoxy-1-(indol-4-yloxy)-propane and 2-(3-nitroxybutanoylamino)-ethyl amine | 31 | 163 (ethanol) |
| 68. | 1-(1,2-dihydro-2-oxoquinolin-5-yloxy)-3-[2-(3-nitroxy-butanoylamino)-ethylamino]-propan-2-ol hemifumarate from 1-(1,2-dihydro-2-oxo-quinolin-5-yloxy)-2,3-epoxy-propane and 2-(3-nitroxy-butanoylamino)-ethylamine | 30 | 162 (ethanol) |
| 69. | 3-[2-(3-nitroxybutanoylamino)-ethylamino]-1-(1,2,3,4-tetra-hydro-2-oxoquinolin-5-yloxy)-propan-2-ol fumarate from 2,3-epoxy-1-(1,2,3,4-tetrahydro-2-oxoquinolin-5-yloxy)-propane and 2-(3-nitroxybutanoylamino)-ethyl-amine | 51 | 145–146 (ethanol) |
| 70. | 3-[2-(2,2-dimethyl-3-nitroxy- | 28 | 148–149 |

-continued

| | designation | yield % | melting point °C. (solvent) |
|---|---|---|---|
| | propanoylamino)-ethylamino]-1-(1,2,3,4-tetrahydro-2-oxo-quinolin-5-yloxy)-propan-2-ol fumarate from 2,3-epoxy-1-(1,2,3,4-tetrahydro-2-oxoquinolin-5-yloxy)-propane and 2-(2,2-dimethyl-3-nitroxypropanoyl-amino)-ethylamine | | (ethanol) |
| 71. | 1-(2-cyanophenoxy)-3-[2-(4-nitroxybutanoylamino)-ethyl-amino]-propan-2-ol from 1-(2-cyanophenoxy)-2,3-epoxypropane and 2-(4-nitroxybutanoylamino)-ethyl-amine | 20 | 108–110 (ethyl acetate) |
| 72. | 1-(2-allylphenoxy)-3-[1,1-dimethyl-2-(4-nitroxy-butanoylamino)-ethylamino]-propan-2-ol cyclamate from 1-(2-allylphenoxy)-2,3-epoxypropane and 1,1-dimethyl-2-(4-nitroxybutanoylamino)-ethylamine | 33 | 125–127 (ethyl |
| 73. | 3-[1,1-dimethyl-2-(4-nitroxy-butanoylamino)-ethylamino]-1-(1-naphthyloxy)-propan-2-ol fumarate from 2,3-epoxy-1-(1-naphthyl-oxy)-propane and 1,1-dimethyl-2-(4-nitroxybutanoylamino)-ethylamine | 47 | 115–118 (ethyl acetate) |
| 74. | 1-(3-cyanoindol-4-yloxy)-3-[3-(4-nitroxybutanoylamino)-propylamino]-propan-2-ol cyclamate from 1-(3-cyanoindol-4-yloxy)-2,3-epoxypropane and 3-(4-nitroxy-butanoylamino)-propylamine | 22 | 137–138 (ethanol) |
| 75. | 1-(2-cyanophenoxy)-3-[2-(5-nitroxypentanoylamino)-ethyl-amino]-propan-2-ol fumarate from 1-(2-cyanophenoxy)-2,3-epoxypropane and 2-(5-nitroxypentanoylamino)-ethylamine | 31 | 125–128 (acetone) |
| 76. | 1-(1-napthyloxy)-3-[2-(5 nitroxypentanoylamino)-ethyl-amino]-propan-2-ol from 2,3-epoxy-1-(1-naphthyl-oxy)-propane and 2-(5-nitroxy-pentanoylamino)-ethylamine | 49 | 92–95 (ethyl acetate) |
| 77. | 1-(indol-4-yloxy)-3-[2-(5-nitroxypentanoylamino)-ethyl-amino]-propan-2-ol hemi-fumarate from 2,3-epoxy-1-(indol-4-yloxy)-propane and 2-(5-nitroxypentanoylamino)-ethylamine | 46 | 127–129 (ethanol) |
| 78. | 1-(6-methylindol-4-yloxy)-3-[2-(5-nitroxypentanoylamino)-ethylamino]-propan-2-ol cyclamate from 2,3-epoxy-1-(6-methyl-indol-4-yloxy)-propane and 2-(5-nitroxypentanoylamino)-ethylamine | 37 | 150–151 (ethanol) |
| 79. | 3-[2-(5-nitroxypentanoyl-amino)-ethylamino]-1-(1,2,3,4-tetrahydro-2-oxoquinolin-5-yloxy)-propan-2-ol fumarate from 2,3-epoxy-1-(1,2,3,4-tetrahydro-2-oxoquinolin-5-yloxy)-propane and 2-(5-nitroxypentanoylamino)-ethylamine | 53 | 153–155 (ethanol) |
| 80. | trans.-1-(2-allyloxyphenoxy)-3-[2-[(2-nitroxycyclohexyl)-acetylamino]-ethylamino]- | 33 | 105–107 (ethyl acetate) |

| designation | yield % | melting point °C. (solvent) |
|---|---|---|
| propan-2-ol from 1-(2-allyloxyphenoxy)-2,3-epoxypropane and trans-2-[(2-nitroxycyclohexyl)-acetylamino]-ethylamine | | |
| 81. trans-1-(2-cyanophenoxy)-3-[2-[(2-nitroxycyclohexyl)-acetylamino]-ethylamino]-propan-2-ol fumarate from 1-(2-cyanophenoxy)-2,3-epoxypropane and trans-2-[(2-nitroxycyclohexyl)-acetylamino]-ethylamine | 38 | 145–148 (ethyl acetate) |
| 82. trans-1-(2-chloro-5-methylphenoxy)-3-[2-[(2-nitroxycyclohexyl)-acetylamino]-ethylamino]-propan-2-ol fumarate from 1-(2-chloro-5-methylphenoxy)-2,3-epoxypropane and trans-2-[(2-nitroxycyclohexyl)-acetylamino]-ethylamine | 35 | 148–150 (acetone) |
| 83. trans-1-(4-methylcarbonyloxy-2,3,5-trimethylphenoxy)-3-[2-[(2-nitroxycyclohexyl)-acetylamino]-ethylamino]-propan-2-ol from 2,3-epoxy-1-(4-methylcarbonyloxy-2,3,5-trimethylphenoxy)-propane and trans-2-[(2-nitroxycyclohexyl)-acetylamino]-ethylamine | 25 | 80–83 (ethyl acetate) |
| 84. trans-1-(1-naphthyloxy)-3-[2-[(2-nitroxycyclohexyl)-acetylamino]-ethylamino]-propan-2-ol fumarate from 2,3-epoxy-1-(1-naphthyloxy)-propane and trans-2-[(2-nitroxycyclohexyl)-acetylamino]-ethylamine | 63 | 154–156 (ethyl acetate) |
| 85. trans-1-(indol-4-yloxy)-3-[2-[(2-nitroxycyclohexyl)-acetylamino]-ethylamino]-propan-2-ol hemifumarate from 2,3-epoxy-1-(indol-4-yloxy)-propane and trans-2-[(2-nitroxycyclohexyl)-acetylamino]-ethylamine | 26 | 139–141 (ethanol) |
| 86. trans-3-[2-[(2-nitroxycyclohexyl)-acetylamino]-ethylamino]-1-(1,2,3,4-tetrahydro-2-oxoquinolin-5-yloxy)-propan-2-ol fumarate from 2,3-epoxy-1-(1,2,3,4-tetrahydro-2-oxoquinolin-5-yloxy)-propane and trans-2-[(2-nitroxycyclohexyl)-acetylamino]-ethylamine | 38 | 133 (ethanol) |
| 87. trans-1-(1,2-dihydro-2-oxoquinolin-5-yloxy)-3-[2-[(2-nitroxycyclohexyl)-acetylamino]-ethylamino]-propan-2-ol fumarate from 1-(1,2-dihydro-2-oxoquinolin-5-yloxy)-2,3-epoxypropane and trans-2-[(2-nitroxycyclohexyl)-acetylamino]-ethylamine | 25 | 128–130 (ethanol) |
| 88. 3-[2-(2-methyl-4-nitroxybutanoylamino)-1-(2-oxoindolin-4-yloxy)-propan-2-ol cyclamate from 2,3-epoxy-1-(2-oxoindolin-4-yloxy)-propane and 2-(2-methyl-4-nitroxybutanoylamino)-ethylamine | 17 | 123–125 (ethanol) |
| 89. 1-(2-allylphenoxy)-3-[2-[(2-nitroxyethoxy)-acetylamino)-ethylamino]-propan-2-ol fumarate from 1-(2-allylphenoxy)-2,3-epoxypropane and 2-[(2-nitroxy- | 12 | 128 (acetone) |
| ethoxy)-acetylamino]-ethylamine | | |

EXAMPLE 3

2-(3-Hydroxybutanoylamino)-ethylamine 192 ml. 1,2-diaminoethane are mixed with 60 ml. water and, with stirring and gentle cooling at 20°–30° C., 74 ml. β-butyrolactone are added dropwise thereto. After 4 days, the reaction mixture is distilled off in a vacuum and the crystal slurry obtained is dried over sulphuric acid in a desiccator. There are obtained 122.4 g. (93% of theory) of the desired base; m.p. 71°–73° C.

EXAMPLE 4

The following compounds are obtained in a manner analogous to that described in Example 3:

| designation | yield % | melting point °C. (solvent) |
|---|---|---|
| 1. 2-(4-hydroxybutanoylamino)-ethylammonium oxalate from γ-butyrolactone and 1,2-diaminoethane | 93 | 65–66 (propan-2-ol) |
| 2. 2-(5-hydroxypentanoylamino)-ethylammonium oxalate from δ-valerolactone and 1,2-diaminoethane | 78 | 75 (propan-2-ol) |
| 3. 2-(2,4-dihydroxy-3,3-dimethylbutanoylamino)-ethylammonium oxalate from 2-hydroxy-3,3-dimethyl-γ-butyrolactone and 1,2-diaminoethane | 80 | 187–189 (propan-2-ol) |
| 4. 3-(4-hydroxybutanoylamino)-propylammonium oxalate from γ-butyrolactone and 1,3-diaminopropane | 52 | 80 (propan-2-ol) |
| 5. 3-(4-hydroxybutanoylamino)-2,2-dimethylpropylammonium oxalate from γ-butyrolactone and 1,3-diamino-2,2-dimethylpropane | 62 | 127–130 (propan-2-ol) |
| 6. 2-(4-hydroxypentanoylamino)-ethylammonium oxalate from γ-valerolactone and 1,2-diaminoethane | 78 | 75 (propan-2-ol) |
| 7. trans-2-[(2-hydroxycyclohexyl)-acetylamino]-ethylamine from trans-(2-hydroxycyclohexyl)-acetic acid lactone (see J. Am. Chem. Soc., 67, 233/1945) and 1,2-diaminoethane | 88 | 136–137 (propan-2-ol) |
| 8. 1,1-dimethyl-2-(4-hydroxybutanoylamino)-ethylammonium oxalate from γ-butyrolactone and 1,2-diamino-2-methylpropane | 41 | 179–180 (propan-2-ol/ ethyl acetate 1:2 v/v) |
| 9. 2-(3,3-dimethyl-5-hydroxypentanoylamino)-ethylammonium oxalate from 3,3-dimethyl-δ-valerolactone (prepared from 3,3-dimethylglutaric acid anhydride; see J. Org. Chem. 35, 3574/1970) and 1,2-diaminoethane | 63 | 124–126 (propan-2-ol) |
| 10. trans-1,1-dimethyl-2-[(2-hydroxycyclohexyl)-acetylamino]-ethylammonium oxalate from trans-(2-hydroxycyclohexyl)-acetic acid lactone and 1,2-diamino-2-methylpropane | 64 | 210–212 (propan-2-ol/ diethyl ether 2:1 v/v) |
| 11. 1,1-dimethyl-2-(3-hydroxybutanoylamino)-ethylammonium oxalate | 78 | 142–145 (propan-2-ol/ ethyl |

-continued

| designation | yield % | melting point °C. (solvent) |
|---|---|---|
| from β-butyrolactone and 1,2-diamino-2-methylpropane | | acetate 1:4 v/v |
| 12. 2-(4-hydroxy-2-methylbutanoyl-amino)-ethylammonium oxalate from 2-methyl-γ-butyrolactone and 1,2-diaminoethane | 75 | 103–106 (methanol/ethyl acetate) |
| 13. 2-(2,2-dimethyl-3-hydroxy-propanoylamino)-ethylammonium oxalate from methyl 2,2-dimethyl-3-hydroxypropionate and 1,2-diaminoethane | 78 | 168–170 (propan-2-ol) |
| 14. 2-[(2-hydroxyethoxy)-acetyl-amino]-ethylammonium oxalate from ethyl 2-(2-hydroxyethoxy)-acetate (see Chem. Ber., 93-, 1129/1960) and 1,2-diamino-ethane | 89 | 123–124 (propan-2-ol) |

EXAMPLE 5

2-(3-Nitroxybutanoylamino)-ethylamine 30 g. 2-(3-Hydroxybutanoylamino)-ethylamine are slowly introduced, with stirring at 5° to 10° C., into 100% nitric acid. After stirring for 2 hours at 0° to 5° C., the reaction solution is stirred into 1 liter of ice-cooled anhydrous diethyl ether, the supernatant ethereal layer is decanted off, the separated oil is covered with methylene chloride and the base is liberated with sodium carbonate. After suction filtration and evaporation in a vacuum at a maximum bath temperature of 20° C., there are obtained 33 g. (84% of theory) of base in the form of an oil.

EXAMPLE 6

The following compounds are obtained in a manner analogous to that described in Example 5:

| designation | yield % | melting point °C. (solvent) |
|---|---|---|
| 1. 2-(4-nitroxybutanoylamino)-ethylammonium oxalate from 2-(4-hydroxybutanoyl-amino)-ethylamine and nitric acid | 95 | oil |
| 2. 2-(5-nitroxypentaoylamino)-ethylamine from 2-(5-hydroxypentanoyl-amino)-ethylammonium oxalate and nitric acid | 76 | oil |
| 3. 2-(3,3-dimethyl-2,4-dinitroxy-butanoylamino)-ethylammonium nitrate from 2-(2,4-dihydroxy-3,3-dimethylbutanoylamino)-ethyl-amine and nitric acid | 70 | 158–160 ethyl acetate/diethyl ether |
| 4. 3-(4-nitroxybutanoylamino)-propylamine from 3-(4-hydroxybutanoyl-amino)-propylammonium oxalate and nitric acid | 73 | oil |
| 5. 2,2-dimethyl-3-(4-nitroxy-butanoylamino)-propylamine from 2,2-dimethyl-3-(4-hydroxybutanoylamino)-propyl-ammonium oxalate and nitric acid | 60 | oil |
| 6. 2-(4-nitroxypentanoylamino)-ethylamine from 2-(4-hydroxypentanoyl-amino)-ethylamine and nitric acid | 76 | oil |
| 7. trans-2-[(2-nitroxycyclohexyl)-acetylamino]-ethylamine from trans-2-[(2-hydroxycyclo-hexyl)-acetylamino]-ethylamine and nitric acid | 45 | oil |
| 8. 1,1-dimethyl-2-(4-nitroxy-butanoylamino)-ethylamine from 1,1-dimethyl-2-(4-hydroxy-butanoylamino)-ethylammonium oxalate and nitric acid | 100 | oil |
| 9. 2-(3,3-dimethyl-5-nitroxy pentanoylamino)-ethylamine from 2-(3,3-dimethyl-5-hydroxy-pentanoylamino)-ethylammonium oxalate and nitric acid | 86 | oil |
| 10. trans-1,1-dimethyl-2-[(2-nitroxycyclohexyl)-acetylamino]-ethylamine from trans-1,1-dimethyl-2-[(2-hydroxycyclohexyl)-acetyl-amino]-ethylammonium oxalate and nitric acid | 99 | oil |
| 11. 1,1-dimethyl-2-(3-nitroxy-butanoylamino)-ethylamine from 1,1-dimethyl-2-(3-hydroxy-butanoylamino)-ethylammonium oxalate and nitric acid | 93 | oil |
| 12. 2-(2-methyl-4-nitroxy-butanoylamino)-ethylamine from 2-(4-hydroxy-2-methyl-butanoylamino)-ethylammonium oxalate and nitric acid | 70 | oil |
| 13. 2-(2,2-dimethyl-3-nitroxy-propanoylamino)-ethylamine from 2-(2,2-dimethyl-3-hydroxy-propanoylamino)-ethylammonium oxalate and nitric acid | 100 | oil |
| 14. 2-[(2-nitroxyethoxy)-acetyl-amino]-ethylamine from 2-[-(2-hydroxyethoxy)-acetylamino]-ethylammonium oxalate and nitric acid | 68 | oil |

EXAMPLE 7

3-[1,1-Dimethyl-2-(2,2-dimethyl-3-nitroxy-propanoylamino)-ethylamino]-1-(3-methylben-zimidazol-4-yloxy)-propan-2-ol fumarate A solution of 1.4 g. 2,2-dimethyl-3-nitroxypropanoyl chloride in 50 ml. dry tetrahydrofuran is added dropwise at ambient temperature to a solution of 2.3 g. 3-(2-amino-1,1-dimethylethylamino)-1-(3-methylben-zimidazol-4-yloxy)-propan-2-ol in 150 ml. dry tetrahydrofuran, followed by further stirring for 2 hours. The reaction mixture is evaporated and chromatographed on silica gel with methylene chloride/methanol (4:2 v/v). The product obtained (2.0 g.) is dissolved in 60 ml. methylene chloride and mixed with 0.54 g. fumaric acid in 100 ml. acetone. The precipitate which separates out after the addition of 200 ml. diethyl ether is filtered off with suction and dried. There are obtained 2.3 g. (53% of theory) of the desired product in the form of crystals; m.p. 187°–190° C.

EXAMPLE 8

In a manner analogous to that described in Example 7, from appropriate 1-aryloxy-3-(2-amino-1,1-dime-thylethylamino)-propan-2-ols or 1-hetaryloxy-3-(2-amino-1,1-dimethylethylamino)-propan-2-ols and ni-troxyalkanoyl chlorides, there are obtained the following compounds:

| designation | yield % | melting point °C. (solvent) |
|---|---|---|
| 1. 3-[1,1-dimethyl-2-(2,2-dimethyl-3-nitroxypropanoylamino)-ethylamino]-1-[4-(2-methoxyethyl)-phenoxy]-propan-2-ol from 3-(2-amino-1,1-dimethyl-ethylamino)-1-[4-(2-methoxy-ethyl)-phenoxy]-propan-2-ol and 2,2-dimethyl-3-nitroxypropanoyl chloride | 41 | oil |
| 2. 1-(2-cyclopentylphenoxy)-3-[1,1-dimethyl-2-(2,2-dimethyl-3-nitroxypropanoylamino)-ethylamino]-propan-2-ol from 3-(2-amino-1,1-dimethyl-ethylamino)-1-(2-cyclopentyl-phenoxy)-propan-2-ol and 2,2-dimethyl-3-nitroxypropanoyl chloride | 45 | 138–140 (ethyl acetate/ diethyl ether 2:3 v/v) |
| 3. 1-(4-carbamoylmethylphenoxy)-3-[1,1-dimethyl-2-[2,2-bis-(nitroxymethyl)-propanoyl-amino]-ethylamino]-propan-2-ol from 3-(2-amino-1,1-dimethyl-ethylamino)-1-(4-carbamoyl-methylphenoxy)-propan-2-ol and 2,2-bis-(nitroxymethyl)-propanoyl chloride | 48 | amorphous (diethyl ether) |
| 4. 1-(4-cyclohexylaminocarbonyl-aminophenoxy)-3-[1,1-dimethyl-2-(2,2-dimethyl-3-nitroxy-propanoylamino)-ethylamino]-propan-2-ol from 3-(2-amino-1,1-dimethyl-ethylamino)-1-(4-cyclohexyl-aminocarbonylaminophenoxy)-propan-2-ol and 2,2-dimethyl-3-nitroxypropanoyl chloride | 25 | 172–175 (diethyl ether/ ligroin 1:1 v/v) |
| 5. 3-[1,1-dimethyl-2-(2,2-dimethyl-3-nitroxypropanoylamino)-ethylamino]-1-(4-methylcarbonyloxy-2,3,5-trimethylphenoxy)-propan-2-ol fumarate from 3-(2-amino-1,1-dimethyl-ethylamino)-1-(4-methylcarbonyl-oxy-2,3,5-trimethylphenoxy)-propan-2-ol and 2,2-dimethyl-3-nitroxypropanoyl chloride | 84 | 68–70 (acetone) |
| 6. 3-[1,1-dimethyl-2-(2,2-dimethyl-3-nitroxypropanoylamino)-ethylamino]-1-(4-hydroxy-2,3,5-trimethylphenoxy)-propan-2-ol fumarate from 3-(2-amino-1,1-dimethyl-ethylamino)-1-(4-hydroxy-2,3,5-trimethylphenoxy)-propan-2-ol and 2,2-dimethyl-3-nitroxy-propanoyl chloride | 24 | 152–155 (diethyl ether) |
| 7. 1-(benzimidazolin-2-on-4-yloxy)-3-[1,1-dimethyl-2-(2,2-dimethyl-3-nitroxypropanoylamino)-ethylamino]-propan-2-ol fumarate from 3-(2-amino-1,1-dimethyl-ethylamino)-1-(benzimidazolin-2-on-4-yloxy)-propan-2-ol and 2,2-dimethyl-3-nitroxypropanoyl chloride | 69 | 118–120 (diethyl ether) |
| 8. 1-(carbazol-4-yloxy)3-[1,1-dimethyl-2-(2,2-dimethyl-3-nitroxypropanoylamino)-ethylamino]-propan-2-ol fumarate from 3-(2-amino-1,1-dimethyl-ethylamino)-1-(carbazol-4-yloxy)-propan-2-ol and 2,2-dimethyl-3-nitroxypropanoyl chloride | 34 | 185–186 (diethyl ether) |
| 9. 3-[2-(2,2-bis(nitroxymethyl)-propanoylamino]-1,1-dimethyl-ethylamino]-1-(4-cyclohexyl-aminocarbonylaminophenoxy)-propan-2-ol fumarate from 3-(2-amino-1,1-dimethyl-ethylamino)-1-(4-cyclohexyl-aminocarbonylaminophenoxy)-propan-2-ol and 2,2-bis-(nitroxymethyl)-propanoyl chloride | 37 | 174–176 (diethyl ether) |
| 10. 3-[2-(2,2-bis-(nitroxymethyl)-propanoylamino]-1,1-dimethyl-ethylamino]-1-(3-methylbenz-imidazol-4-yloxy)-propan-2-ol fumarate from 3-(2-amino-1,1-dimethyl-ethylamino)-1-(3-methylbenz-imidazol-4-yloxy)-propan-2-ol and 2,2-bis-(nitroxymethyl)-propanoyl chloride | 24 | 105–108 (diethyl ether) |
| 11. 3-[2-[2,2-bis-(nitroxymethyl)-propanoylamino]-1,1-dimethyl-ethylamino]-1-(carbazol-4-yloxy)-propan-2-ol fumarate from 3-(2-amino-1,1-dimethyl ethylamino)-1-(carbazol-4-yloxy)-propan-2-ol and 2,2-bis-(nitroxy-methyl)-propanoyl chloride | 34 | 110–115 (diethyl ether) |
| 12. 3-[1,1-dimethyl-2-(4-nitroxy-butanoylamino)-ethylamino]-1-[4-(2-methoxyethyl)-phenoxy]-propan-2-ol from 3-(2-amino-1,1-dimethyl-ethylamino)-1-[4-(2-methoxy-ethyl)-phenoxy]-propan-2-ol and 4-nitroxybutanoyl chloride | 100 | oil |
| 13. 1-(2-cyclopentylphenoxy)-3-[1,1-dimethyl-2-(4-nitroxybutanoyl-amino)-ethylamino]-propan-2-ol cyclamate from 3-(2-amino-1,1-dimethyl-ethylamino)-1-(2-cyclopentyl-phenoxy)-propan-2-ol and 4-nitroxybutanoyl chloride | 40 | 127–128 (ethyl acetate/ diethyl ether 1:9 v/v) |
| 14. 1-(4-cyclohexylaminocarbonyl-aminophenoxy)-3-[1,1-dimethyl-2-(4-nitroxybutanoylamino)-ethylamino]-propan-2-ol fumarate from 3-(2-amino-1,1-dimethyl-ethylamino)-1-(4-cyclohexyl-aminocarbonylaminophenoxy)-propan-2-ol and 4-nitroxy-butanoyl chloride | 36 | 177–179 (diethyl ether) |
| 15. 3-[1,1-dimethyl-2-(4-nitroxy-butanoylamino)-ethylamino]-1-(4-methylcarbonyloxy-2,3,5-trimethylphenoxy)-propan-2-ol fumarate from 3-(2-amino-1,1-dimethyl-ethylamino)-1-(4-methyl-carbonyloxy-2,3,5-trimethyl-phenoxy)-propan-2-ol and 4-nitroxybutanoyl chloride | 51 | 73–75 (diethyl ether) |
| 16. 3-[1,1-dimethyl-2-(4-nitroxy-butanoylamino)-ethylamino]-1-(4-hydroxy-2,3,5-trimethyl-phenoxy)-propan-2-ol cyclamate from 3-(2-amino-1,1-dimethyl-ethylamino)-1-(4-hydroxy-2,3,5-trimethylphenoxy)-propan-2-ol and 4-nitroxybutanoyl chloride | 26 | 133–134 (ethyl acetate) |
| 17. 1-(benzimidazolin-2-on-4-yloxy)-3-[1,1-dimethyl-2-(4-nitroxy-butanoylamino)-ethylamino]-propan-2-ol fumarate from 3-(2-amino-1,1-dimethyl-ethylamino)-1-(benzimidazolin-2-on-4-yloxy)-propan-2-ol and 4-nitroxybutanoyl chloride | 37 | 105–107 (diethyl ether) |
| 18. 1-(2-cyanophenoxy)-3-[2-(2,2-dimethyl-3-nitroxypropanoyl-amino)-ethylamino]-propan-2-ol fumarate | 16 | 136–138 (diethyl ether) |

| designation | yield % | melting point °C. (solvent) |
| --- | --- | --- |
| from 3-(2-aminoethylamino)-1-(2-cyanophenoxy)-propan-2-ol and 2,2-dimethyl-3-nitroxypropanoyl chloride | | |
| 19. 3-[2-(2,2-dimethyl-3-nitroxypropanoylamino)-ethylamino]-1-(1-naphthyloxy)-propan-2-ol cyclamate from 3-(2-aminoethylamino)-1-(1-naphthyloxy)propan-2-ol and 2,2-dimethyl-3-nitroxypropanoyl chloride | 6 | 107–109 (ethyl acetate) |
| 20. 3-[2-(2,2-dimethyl-3-nitroxypropanoylamino)-ethylamino-1-(2-oxoindolin-4-yloxy)-propan-2-ol hemifumarate from 3-(2-aminoethylamino)-1-(2-oxoindolin-4-yloxy)-propan-2-ol and 2,2-dimethyl-3-nitroxypropanoyl chloride | 10 | 180–183 (methanol) |

3-(2-Amino-1,1-dimethylethylamino)-1-(4-hydroxy-2,3,5-trimethylphenoxy)-propan-2-ol is obtained from 3-(2-dibenzylamino-1,1-dimethylethylamino)-1-(4-methyl-carbonyloxy-2,3,5-trimethylphenoxy)-propan-2-ol by saponification with potassium hydroxide in ethanol and subsequent hydrogenation over palladium-charcoal (10%) in ethanol at 60° C.

3-(2-Aminoethylamino)-1-aryloxypropan-2-ols are prepared by reaction of the appropriate 1-aryloxy-2,3-epoxypropanes with excess 1,2-diaminoethane.

EXAMPLE 9

3-(2-Amino-1,1-dimethylethylamino)-1-(3-methylbenzimidazol-4-yloxy)-propan-2-ol 10.2 g. 2,3-Epoxy-1-(3-methylbenzimidazol-4-yloxy)-propane are added to 40.3 g. 2-dibenzylamino-1,1-dimethylethylamine (prepared analogously to H. G. Johnson, J.A.C.S., 68, 12/1946) in 300 ml. ethanol and the reaction mixture is stirred for 3 days at ambient temperature. The reaction mixture is now hydrogenated at 60° C. over 8 g. palladium-charcoal (10%) until the take up of hydrogen is finished. The catalyst is then filtered off with suction and the filtrate evaporated to dryness. The residue is chromatographed on silica gel with methanol/concentrated aqueous ammonia solution (95:5 v/v). The appropriate fractions are evaporated, the residue is taken up in methylene chloride and dried over anhydrous sodium sulphate and the solution is evaporated to dryness. There are obtained 8.7 g. (66% of theory) of the desired product as a pale yellow oil.

EXAMPLE 10

In a manner analogous to that described in Example 9, from 1-aryloxy-2,3-epoxypropanes or 1-hetaryloxy-2,3-epoxypropanes and 2-dibenzylamino-1,1-dimethylethylamine, there are obtained the following compounds:

| designation | yield % | melting point °C. (solvent) |
| --- | --- | --- |
| 1. 3-(2-amino-1,1-dimethylethyl-amino)-1-[4-(2-methoxyethyl)-phenoxy]-propan-2-ol from 2,3-epoxy-1-[4-(2-methoxyethyl)-phenyl)-phenoxypropane | 37 | pale yellow oil |
| 2. 3-(2-amino-1,1-dimethylethyl-amino)-1-(2-cyclopentyl-phenoxy)-propan-2-ol from 1-(2-cyclopentylphenoxy)-2,3-epoxypropane | 43 | yellow oil |
| 3. 3-(2-amino-1,1-dimethylethyl-amino)-1-(4-cyclohexylamino-carbonylaminophenoxy)-propan-2-ol from 1-(4-cyclohexylamino-carbonylaminophenoxy)-2,3-epoxypropane | 33 | 162–163 (diethyl ether) |
| 4. 3-(2-amino-1,1-dimethylethyl-amino)-1-(4-methylcarbonyloxy-2,3,5-trimethylphenoxy)-propan-2-ol from 2,3-epoxy-1-(4-methyl-carbonyloxy-2,3,5-trimethyl-phenoxy)-propane | 25 | pale yellow oil |
| 5. 3-(2-amino-1,1-dimethylethyl-amino)-1-(benzimidazolin-2-on-4-yloxy)-propan-2-ol from 1-(2-amino-3-nitrophenyl-oxy)-2,3-epoxypropane and subsequent hydrogenation and ring closure reaction | 62 | amorphous |
| 6. 3-(2-amino-1,1-dimethylethyl-amino)-1-(carbazol-4-yloxy)-propan-2-ol from 1-(carbazol-4-yloxy)-2,3-epoxypropane | 43 | amorphous |
| 7. 3-(2-amino-1,1-dimethylethyl-amino)-1-(4-carbamoylmethyl-phenoxy)-propan-2-ol from 1-(4-carbamoylmethyl-phenoxy)-2,3-epoxypropane | 81 | 113–115 (diethyl ether) |

EXAMPLE 11

3-[1,1-Dimethyl-2-[(5-O-nitroisosorbid-2-yloxy)-carbonylamino]-ethylamino]-1-(3-methylbenzimidazol-4-yloxy)-propan-2-ol fumarate A solution of 1.91 g. 5-O-nitroisosorbide (5-O-nitro-1:4,3:6-dianhydrosorbite) and 1.01 g. triethylamine in 10 ml. dry tetrahydrofuran is added dropwise to a solution of 1.63 g. 1,1'-carbonyldiimidazole in 30 ml. dry tetrahydrofuran and the reaction mixture is stirred for 1 hour at ambient temperature. To this solution is added dropwise a solution of 2.92 g. 3-(2-amino-1,1-dimethylethylamino)-1-(3-methylbenzimidazol-4-yloxy)-propan-2-ol in 30 ml. dry tetrahydrofuran, followed by stirring for 1 hour, whereafter the solvent is distilled off. The residue (7.2 g.) is chromatographed on silica gel with methylene chloride/methanol (8:2 v/v). The purified product (3.6 g.) is dissolved in 50 ml. acetone, mixed with 0.81 g. fumaric acid in 50 ml. acetone and the solution is then evaporated to dryness. The residue is digested with 100 ml. diethyl ether, filtered off with suction and dried. There are obtained 3.3 g. (53% of theory) of the desired product in the form of crystals; m.p. 128°–130° C.

EXAMPLE 12

In a manner analogous to that described in Example 5, from 1-aryloxy-3-aminoalkylaminopropan-2-ols or 1-hetaryloxy-3-aminoalkylaminopropan-2-ols and nitroxyalkanols, there are obtained the following compounds:

| designation | yield % | melting point °C. (solvent) |
|---|---|---|
| 1. 3-[1,1-Dimethyl-2-[(5-O—nitro-isosorbid-2-yloxy)-carbonyl-amino]-ethylamino]-1-[4-(2-methoxyethyl)-phenoxy]-propan-2-ol cyclamate from 3-[(amino-1,1-dimethyl)-ethylamino]-1-[4-(2-methoxy-ethyl)-phenoxy]-propan-2-ol and 5-O—nitroisosorbide | 35 | 82 (acetone) |
| 2. 3-[1,1-dimethyl-2-[(5-O—nitro-isosorbid-2-yloxy)-carbonyl-amino]-ethylamino]-1-(4-methyl-carbonyloxy-2,3,5-trimethyl-phenoxy)-propan-2-ol from 3-(2-amino-1,1-dimethyl-ethylamino)-1-(4-methylcarbonyl-oxy-2,3,5-trimethylphenoxy)-propan-2-ol and 5-O—nitroiso-sorbide | 91 | amorphous |
| 3. 1-(4-carbamoylmethylphenoxy)-3-[1,1-dimethyl-2-[(5-O—nitroiso-sorbid-2-yloxy)-carbonylamino]-ethylamino]-propan-2-ol from 3-(2-amino-1,1-dimethyl-ethylamino)-1-(4-carbamoyl-methylphenoxy)-propan-2-ol and 5-O—nitroisosorbide | 78 | oil |

EXAMPLE 13

1-(2-Chloro-5-methylphenoxy)-3-[2-[(3-nitroxy-propylamino)-carbonylamino]-ethylamino]-propan-2-ol.

3.1 g. 1-(2-Chloro-5-methylphenoxy)-2,3-epoxypropane and 8.5 g. 2-[(3-nitroxypropylamino)-carbonylamino]-ethylamine in 100 ml. n-butanol are stirred at ambient temperature for 18 hours. The solvent is distilled off at 30° C. bath temperature under oil pump vacuum, the residue is dissolved in 150 ml. ethyl acetate and this solution is washed 4 times with 60 ml. amounts of water. The organic phase is dried and evaporated and the residue is chromatographed on silica gel with methylene chloride/methanol (6:4 v/v). The appropriate fractions are evaporated and the residue is triturated with diethyl ether, filtered off with suction and dried. There are obtained 2.2 g. (35% of theory) of the desired product in the form of crystals; m.p. 109°–111° C.

The 2-[(3-Nitroxypropylamino)-carbonylamino]ethylamine used as starting material is prepared in the following way: 140 g. tetrahydro-2H-1,3-oxazin-2-one (see J. Org. Chem., 24, 1788/1959) and 270.5 g. 1,2-diaminoethane are stirred in an autoclave under an atmosphere of nitrogen of 50 bar for 8 hours at 100° C. Excess 1,2-diaminoethane is removed under oil pump vacuum and the oily residue is dissolved in 2.6 liters boiling propan-2-ol. A hot solution of 117.3 g. oxalic acid in 1.3 liters propan-2-ol is added to this solution. The solution is allowed to cool and then filtered off with suction. There are obtained 215.5 g. (66% of theory) of white crystals of 2-[(3-hydroxypropylamino)-carbonylamino]-ethylammonium oxalate; m.p. 160°–163° C.

25.1 g. of this oxalate are introduced at −20° to −17° C., within the course of 20 minutes, into 100% nitric acid. The reaction mixture is stirred for 30 minutes at −20° C. and then poured into 1 liter cold diethyl ether. The solution is decanted and the residue is dissolved in 150 ml. water. By the addition of sodium carbonate, the pH value is adjusted to 10. 1 liter of methylene chloride are added thereto and, while stirring, sodium carbonate is added up to saturation. The solid material is filtered off with suction, washed with methylene chloride and the filtrate evaporated. There are obtained 8.5 g. of yellow oil (41% of theory).

EXAMPLE 14

1-(1-Naphthyloxy)-3-[2-[(4-nitroxy-1-piperidino)car-bonylamino]-ethylamino]-propan-2-ol fumarate.

0.4 g. 2,3-Epoxy-1-(1-naphthyloxy)-propane and 1.4 g. 2-[(4-nitroxy-1-piperidino)-carbonylamino]ethylamine are stirred in 30 ml. n-butanol for 15 hours at ambient temperature. The solvent is then distilled off, the residue is taken up in 50 ml. ethyl acetate and this solution is washed 3 times with 50 ml. amounts of water. The organic phase is dried and evaporated and the residue (1.2 g. oil) is chromatographed on silica gel with methylene chloride/methanol (8:2 v/v). The appropriate fractions are evaporated and the residue (0.6 g.) is dissolved in 15 ml. ethyl acetate and mixed with 0.16 g. fumaric acid. The precipitate which separates is filtered off with suction and dried. There is obtained 0.22 g. (6% of theory) of the desired product in the form of white crystals; m.p. 123°–125° C.

The 2-[(4-nitroxy-1-piperidino)-carbonylamino]ethylamine used as starting material is prepared in the following way: a solution of 1,1′-carbonyldiimidazole in 750 ml. tetrahydrofuran is added drop-wise at 0° to 2° C. to 49.0 g. N,N-dibenzylethylenediamine and 28.25 g. triethylamine in 250 ml. tetrahydrofuran and the reaction mixture is stirred for 1 hour at 0° C. The solution obtained is now added dropwise at 0° to 2° C., within the course of 1.5 hours, into a solution of 20.6 g. 4-hydroxypiperidine in 250 ml. tetrahydrofuran. Stirring is continued for 2 hours at 0° C. and the solution is then allowed to warm up to ambient temperature overnight. After removal of the solvent, the residue is taken up in 0.6 liters ethyl acetate and the solution is washed 3 times with 0.2 liter amounts of water. The organic phase is dried and evaporated.

The residue (69 g.) is chromatographed in silica gel with methylene chloride/methanol (10:1 v/v). There are obtained 39.2 g. (52% of theory) of N,N-dibenzyl-2-[(4-hydroxy-1-piperidino)-carbonylamino]-ethylamine as an oil. 39.1 g. of this oil are dissolved, with warming, in 400 ml. ethanol. 5 g. palladium-charcoal (10%) are added to this solution and the warm solution is hydrogenated, while stirring, up to the end of the take up of hydrogen. The solution is filtered off with suction and evaporated. The oily residue (21.8 g.) is dissolved in 200 ml. boiling propan-2-ol and this solution is mixed with 9.6 g. oxalic acid in 100 ml. boiling propan-2-ol. The solution is allowed to cool and the precipitated crystals are filtered off with suction, washed with ethyl acetate and diethyl ether and dried. There are obtained 22.0 g. (70% of theory) 2-[(4-hydroxy-1-piperidino)-carbonylamino]-ethylamine oxalate (m.p. 173°–175° C.). 5.4 g. of this salt are introduced at −20° C. into 14.4 ml. 100% nitric acid. After 20 minutes, the reaction solution is slowly poured into a cold suspension of 49 g. potassium carbonate in 30 ml. water. The mixture is covered with 0.5 liter methylene chloride and well stirred. The aqueous phase is completely removed by the addition of sodium carbonate and sodium sulphate, whereafter the mixture is filtered with suction and evaporated. There remain 3.0 g. of an oily residue of 2-[(4-nitroxy-1-piperidino)-carbonylamino]-ethylamine.

Experimental Testing

The compounds claimed have beta-blocking as well as nitrate-like properties and can therefore be used as antianginal therapy (heart disorder characterized by attacks of pain where there is an insufficiency of oxygen).

At present pharmaceuticals are available either for their nitrate-like properties, e.g. nitroglycerin, isosorbide dinitrate, isosorbide-5-mononitrate, or for their beta-blocker properties, e.g. propanolol, pindolol. Combinations of these drugs are also used, but so far no compound is available which by its working principle incorporates both qualities. The invention provides compounds which, surprisingly, have nitrate-like as well as beta-blocking qualities in overlapping dosage ranges. Thus, a single compound can be used to treat two separate (but usually related in occurrence) ailments.

Since such substances have so far not been developed specifically, a method for screening the nitrate-like action is not known. It is for this reason that the following method was developed:

(a) to show denitration properties (which constitutes the working principle of all nitrates; see U. Abshagen in Handbook of Experimental Pharmacology, Vol. 76, 1985, Chapter 10.) the denitration rate was evaluated in relation to that of the known isosorbide dinitrate metabolite isosorbide-5-mononitrate ($V_{rel}$). To that end, rats were killed under narcosis and their livers re-perfused 4 min with a corresponding concentrated equimolar ($5 \times 10^{-5}$M/l) solution of isosorbide-5-mononitrate and the substances to be tested respectively (a blood sediment solution was pumped through the liver vessels) and the freed amount in $NO_2$ determined in the perfusate (outflowing fluid). To have comparable conditions, the perfusion with isosorbide-5-mononitrate (standard substance) was administered as control at the second time as if it were an unknown substance (in this way a liver performance change under the test conditions can be recognized and accordingly allowed for).

High $V_{rel}$-values show a fast denitration, low values a slow denitration.

(b) The $\beta$-blocking effectiveness was shown by administering rabbits isoprenaline in an amount of 1 mcg/kg i.v. and determining the dose, which causes an inhibition of 50% of the increase of the frequency through isoprenaline (ID $50_{fcor}$=inhibition dose 50%).

TABLE

| Example | ID$_{50 fcor}$ mg/kg i.V. | $V_{rel}$ |
|---|---|---|
| Isosorbide-5-mononitrate | — | 0,86 |
| Isosorbide-dinitrate | — | 17,5 |
| Propranolol | 331 | — |
| Pindolol | 104 | — |
| 2 (11.) | 279 | 0,95 |
| 2 (17.) | 58 | 0,75 |
| 2 (18.) | 146 | 0,71 |
| 2 (29.) | 96 | 0,86 |
| 2 (31.) | 53 | 0,66 |
| 2 (46.) | 49 | 0,97 |
| 2 (48.) | 74 | 0,94 |
| 2 (72.) | 113 | 0,54 |
| 8 (7.) | 7,9 | 0,96 |
| 8 (15.) | 72 | 1,19 |
| 11 | 62 | 1,23 |

It will be understood that the specification and examples are illustrative but not limitative of the present invention and that other embodiments within the spirit and scope of the invention will suggest themselves to those skilled in the art.

What is claimed is:

1. A compound of the formula

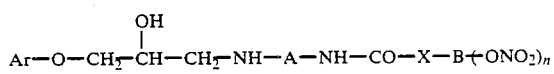

wherein Ar is an indole or indoline which are unsubstituted or substituted one or more times by $C_1$-$C_3$ hydroxyalkyl, formyl, $C_1$-$C_3$ alkanoyl, $C_1$-$C_3$ alkylcarbonylamino, cyano, oxo, hydroxyl, carbamoyl or $C_1$-$C_3$ alkyl, A is a straight-chained or branched $C_1$-$C_8$ alkylene chain, a —$CH_2$— group which can be replaced by a $C_3$-$C_7$ cycloalkylene, B is a straight-chained, mono- or bicyclic, optionally branched, saturated or unsaturated $C_1$-$C_{12}$ alkylene chain, a —$CH_2$— group which can be replaced by a $C_3$-$C_7$ cycloalkylene or up to two —$CH_2$— groups of which each can be replaced by an oxygen or a sulphur atom or by an —S(=O) or —S(=O)$_2$ group, X is a valency bond, an oxygen atom or an —$NR^1$— group, in which $R^1$ is a hydrogen atom or a straight-chained or branched, saturated or unsaturated $C_1$-$C_6$ alkyl or nitroxyalkyl radical or $R^1$, together with the nitrogen atom of the —$NR^1$-group and a —$CH_2$— group of the chain B, can form a $C_4$-$C_6$ heterocyclic ring and n is 1, 2 or 3 or a physiologically acceptable salt thereof with the proviso that when n is 2 or 3 the nitroxy group cannot be geminally substituted.

2. The compound of claim 1, wherein Ar is an indole or indoline which are unsubstituted or substituted one or more times by hydroxyalkyl, formyl, alkanoyl, alkylcarbonylamino, cyano, oxo, hydroxyl, carbamoyl or alkyl, A is a straight-chained or branched $C_1$-$C_8$ alkylene chain, B is a straight-chained or bicyclic, optionally branched, saturated $C_1$-$C_{12}$ alkylene chain, a —$CH_2$— group which can be replaced by a $C_3$-$C_7$ cycloalkylene or up to two —$CH_2$— groups which each can be replaced by an oxygen or a sulphur atom or by an —S(=O) or —S(=O)$_2$ group, X is a valency bond, an oxygen atom or an —$NR^1$— group, wherein $R^1$ is a hydrogen atom, a straight-chained or branched, saturated or unsaturated $C_1$-$C_6$ alkyl or nitroxyalkyl and n is 1 or 2; or a physiologically acceptable salt thereof.

3. The compound of claim 2 wherein Ar is an indole or indoline selected from the group consisting of 2-methyl-4-indolyl,
3-methyl-4-indoly, 6-methyl-4-indolyl, 2-ethyl-4-indolyl,
6-ethyl-4-indolyl, 2,3-dimethyl-4-indolyl,
2,6-dimethyl-4-indolyl, 2-methyl-3-ethyl-4-indolyl,
2-ethyl-3-methyl-4-indolyl, 2,3-diethyl-4-indolyl,
2-cyano-4-indolyl, 3-cyano-4-indolyl,
2-cyano-6-methyl-4-indolyl, 3-cyano-4-indolyl,
2-cyano-6-methyl-4-indolyl,
3-cyano-6-methyl-4-indolyl, 2-carbamoyl-4-indolyl,
3-carbamoyl-4-indolyl, 6-carbamoyl-4-indolyl,
2-carbamoyl-6-methyl-4-indolyl, 2-hydroxymethyl-4-indolyl,
2-hydroxymethyl-5-indolyl, 3-hydroxymethyl-4-indolyl,
2-(2-hydroxyethyl)-4-indolyl, 2-oxoindolin-4-yl,
2-oxoindolin-5-yl, 3-methyl-2-oxo-indolin-4-yl, 3-ethyl-2-oxoindolin-4-yl, 3-isopropyl-2-oxoindolin-4-yl, 3,3-dimethyl-2-oxoindolin-4-yl and 3,3-diethyl-2-oxoindolin-4-yl; A is a straight-chained or branched $C_1$–$C_8$ alkylene chain, B is a straight-chained or branched $C_1$–$C_{12}$ alkylene, X is a valency bond and n is 1, or a physiologically acceptable salt thereof.

4. A physiologically acceptable salt of the compound of claim 1 designated 1-(indol-4-yloxy)-3-[2-(4-nitroxybutanoylamino)ethylamino]-propan-2-ol.

5. A physiologically acceptable salt of the compound of claim 1 designated 3-[2-(4-nitroxybutanoylamino)-ethylamino]-1-(2-oxoindolin-4-yloxy)-propan-2-ol.

6. A physiologically acceptable salt of the compound of claim 1 designated 3-[2-(4-nitroxypentanoylamino)-ethylamino]-1-(2-oxoindolin-4-yloxy)-propan-2-ol.

7. A physiologically acceptable salt of the compound of claim 1 designated 3-[2-(5-nitroxypentanoylamino)-ethylamino]-1-(2-oxoindolin-4-yloxy)-propan-2-ol.

8. A pharmaceutical composition containing an effective amount of the compound of claim 1 for the treatment or prophylaxis of heart and circulatory diseases, in a pharmaceutically acceptable carrier.

9. The pharmaceutical composition of claim 8 wherein said compound is
   3-[2-(4-nitroxybutanoylamino)-ethylamino]-1-(2-oxoindolin-4-yloxy)-propan-2-ol,
   3-[2-(5-nitroxypentanoylamino)-ethylamino]-1-(2-oxoindolin-4-yloxy)-propan-2-ol,
   3-[2-(4-nitroxypentanoylamino)-ethylamino]-1-(2-oxoindolin-4-yloxy)-propan-2-ol or
   1-(indol-4-yloxy)-3-[2-(4-nitroxybutanoylamino)-ethylamino]-propan-2-ol.

10. The pharmaceutical composition of claim 8 containing 10 to 500 mg of said compound.

11. The pharmaceutical composition of claim 10 containing 10 to 200 mg of said compound.

12. A method for treatment of or prophylaxis of heart and circulatory diseases comprising administering an effective amount of the compound of claim 1.

13. The method of claim 12 wherein 5 to 500 mg of the compound are administered.

14. A method for treatment of or prophylaxis of heart and circulatory diseases comprising administering an effective amount of the composition of claim 9.

15. A method for simultaneously producing nitrate-like and beta-blocking effect for the treatment of heart and circulatory diseases comprising administering an effective amount of the compound of claim 1.

* * * * *

UNITED STATES PATENT AND TRADEMARK OFFICE
CERTIFICATE OF CORRECTION

PATENT NO. : 4,863,949

DATED : September 5, 1989

INVENTOR(S) : Herbert Simon, et al.

It is certified that error appears in the above-identified patent and that said Letters Patent is hereby corrected as shown below:

Col. 5, line 11: change "alkylcycanoindolyl" to -- alkylcyanoindolyl --.

Col. 5, line 45: delete "alkyl-1,3-benzodioxol-4-yl" and insert -- alkyl-1,3-benzodioxolyl, preferably 2-methyl-1,3-benzodioxol-4-yl --.

Col. 10, line 12: change "(I)" to -- (I)) --.

Col. 30, entry 72: after "melting point 125-127 (ethyl" insert -- acetate) --.

Signed and Sealed this

Thirtieth Day of April, 1991

Attest:

HARRY F. MANBECK, JR.

Attesting Officer

Commissioner of Patents and Trademarks